(12) United States Patent
Yamaguchi et al.

(10) Patent No.: US 7,001,706 B2
(45) Date of Patent: Feb. 21, 2006

(54) SULFONATE AND A RESIST COMPOSITION

(75) Inventors: Satoshi Yamaguchi, Toyonaka (JP); Makoto Akita, Kusatsu (JP); Isao Yoshida, Ikeda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 10 days.

(21) Appl. No.: 10/892,291

(22) Filed: Jul. 16, 2004

(65) Prior Publication Data

US 2005/0014095 A1   Jan. 20, 2005

(30) Foreign Application Priority Data

Jul. 18, 2003    (JP) .............................. 2003-199026

(51) Int. Cl.
*G03C 1/73* (2006.01)
*G03C 7/039* (2006.01)
*C07C 309/73* (2006.01)

(52) U.S. Cl. .................. 430/270.1; 430/914; 430/921; 430/925; 430/919; 430/923; 430/326; 430/910; 562/54; 562/56

(58) Field of Classification Search ............. 430/270.1, 430/914, 921, 925, 919, 923, 326, 910; 562/54, 562/56
See application file for complete search history.

(56) References Cited

U.S. PATENT DOCUMENTS

| | | | | |
|---|---|---|---|---|
| 5,837,420 | A | 11/1998 | Aoai et al. ............... | 430/270.1 |
| 6,893,794 | B1 * | 5/2005 | Akita et al. .............. | 430/270.1 |
| 2004/0152009 | A1 * | 8/2004 | Yamaguchi et al. ..... | 430/270.1 |

* cited by examiner

Primary Examiner—Sin Lee
(74) Attorney, Agent, or Firm—Birch, Stewart, Kolasch & Birch, LLP

(57) ABSTRACT

A sulfonate of the formula (I):

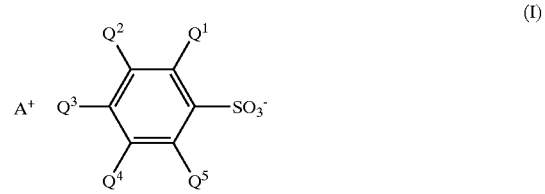

wherein $Q^1$, $Q^2$, $Q^3$, $Q^4$ and $Q^5$ each independently represents a certain substituent, and $A^+$ represents a counter ion, with the proviso that at least one of $Q^1$, $Q^2$, $Q^3$, $Q^4$ and $Q^5$ is a group of the formula (II)

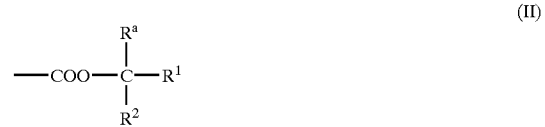

wherein $R^1$ and $R^2$ each independently an alkyl having 1 to 12 carbon atoms or the like; and a chemical amplification type positive resist composition comprising the sulfate of the formula (I) and a resin which contains a structural unit having an acid labile group and which itself is insoluble or poorly soluble in an alkali aqueous solution but becomes soluble in an alkali aqueous solution by the action of an acid.

17 Claims, No Drawings

SULFONATE AND A RESIST COMPOSITION

This nonprovisional application claims priority under 35 U.S.C. § 119(a) on Patent Application No. 2003-199026 filed in JAPAN on Jul. 18, 2003, the entire contents of which are hereby incorporated by reference.

BACKGROUND OF THE INVENTION

1. Field of the Invention

The present invention relates to a novel sulfonate and a resist composition using the same used in fine processing of semiconductors.

2. Related Art

Semiconductor microfabrication usually employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be promising for the next-generation exposure light source. As the exposure light source of the subsequent generation, soft X ray (EUV) having a wavelength of 13 nm or shorter has been proposed. Further, as a lithography technology of somewhat different type from those above, electron beam lithography is energetically studied.

Since light sources having shorter wavelength than that of g line and i line, such as excimer laser and the like have low illumination, it is necessary to enhance the sensitivity of a resist. Consequently, there are used so-called chemical amplification type resists utilizing the catalytic action of an acid produced from a sulfonium salt and the like by exposure and containing a resin having a group being dissociated by this acid.

However, in conventionally known chemical amplification type resist compositions, there is a problem that line edge roughness occurs by generation of standing wave and the like, namely, smoothness on pattern side walls decreases, and resultantly, uniformity of line width deteriorates.

Though it is effective to use an acid generator including anion of benzenesulfonic acid having at least one ester group for positive type photosensitive compositions having higher photosensitivity and less change on standing after exposure, it is still difficult to combine progress of roughness and progress of pattern shapes.

If such resist composition is used as it is in electron beam lithography, there is the problem that throughput in the production of integrated circuits is low for low sensitivity of the resist composition. Though higher sensitivitization of the resist compositions is desired from the viewpoint above, enhancing sensitivity of a resist generally tends to cause deterioration of resolution and deterioration of smoothness of pattern shapes and pattern sidewalls. The edge roughness of patterns is desired to be low because degree of precision for microfabrication is adversely affected if it is high.

SUMMARY OF THE INVENTION

An object of the present invention is to provide a novel sulfonate and to provide a chemical amplification type resist composition comprising the above-mentioned sulfonate and a resin component, and which is suitable for excimer laser lithography using ArF, KrF, or the like, electron beam lithography, and the like, and which shows excellent various resist abilities such as sensitivity, resolution and the like, and giving particularly improved line edge roughness and pattern profiles.

The present invention relates to the followings:

<1> A sulfonate of the formula (I);

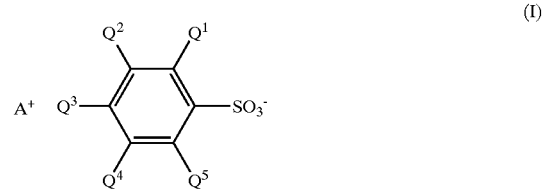

wherein $Q^1$, $Q^2$, $Q^3$, $Q^4$ and $Q^5$ each independently represents a hydrogen, an alkyl having 1 to 16 carbon atoms, an alkoxy having 1 to 16 carbon atoms, a halogen, an aryl having 6 to 12 carbon atoms in which at least one hydrogen may be substituted by an alkyl, a cycloalkyl, an alkoxy, a hydroxyl or a halogen, an arylalkyl having 7 to 12 carbon atoms in which at least one hydrogen on an aryl ring may be substituted by an alkyl, a cycloalkyl, an alkoxy, a hydroxyl or a halogen, a cyano, a mercapto, an alkylthio having 1 to 16 carbon atoms, a hydroxy, a nitro or a group of the formula (I')

—COOR (I')

wherein R represents an aryl having 6 to 12 carbon atoms, a group of the formula (II') or a group of the formula (II")

wherein $R^1$ and $R^2$ each independently represents an alkyl having 1 to 12 carbon atoms, a cycloalkyl having 3 to 12 carbon atoms, an arylalkyl having 7 to 12 carbon atoms or an aryl having 6 to 12 carbon atoms, and at least one hydrogen on an aryl ring in the arylalkyl or in the aryl may be substituted by an alkyl, a cycloalkyl, an alkoxy, a hydroxyl or a halogen, or $R^1$ and $R^2$ bond to form a monocyclic or polycyclic hydrocarbon group together with adjacent —C($R^a$)—, $R^a$ represents an alkyl having 1 to 8 carbon atoms, and —$CH_2$— in the alkyl except the one at the terminal position may be substituted by —CO—, —O— or —S—, $R^3$ and $R^4$ each independently represents a hydrogen, an alkyl having 1 to 6 carbon atoms, a cycloalkyl having 3 to 12 carbon atoms, an aryl having 6 to 12 carbon atoms, an arylalkyl having 7 to 12 carbon atoms, at least one hydrogen on the aryl ring in the aryl or in the arylalkyl may be substituted by an alkyl, a cycloalkyl, an alkoxy, a hydroxyl or a halogen, or $R^3$ and $R^4$ bond to form an monocyclic or polycyclic hydrocarbon group together with adjacent —CH—, with the proviso that at least one of $Q^1$, $Q^2$, $Q^3$, $Q^4$ and $Q^5$ is a group of the formula (II)

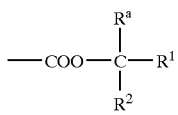

wherein $R^a$, $R^1$ and $R^2$ have the same meaning as described above, and $A^+$ represents a counter ion.

<2> The sulfonate according to <1>, wherein formula (II) is a 1-alkylcycloalkyloxycarbonyl.

<3> The sulfonate according to <2>, wherein the 1-alkyl-cycloalkyloxycarbonyl is a group of the formula (II*)

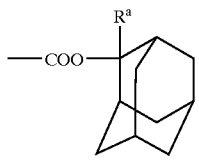

wherein $R^a$ has the same meaning as defined above.

<4> The sulfonate according to <3>, wherein $R^a$ in the formula (II*) is a methyl or an ethyl.

<5> The sulfonate according to any one of <1> to <4>, wherein $A^+$ is a counter ion of the formula (IIa)

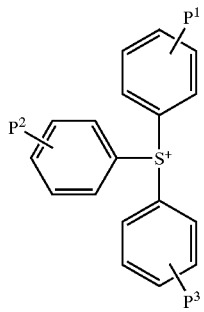

wherein $P^1$, $P^2$ and $P^3$ each independently represents a hydrogen, a hydroxyl, an alkyl having 1 to 6 carbon atoms or an alkoxy having 1 to 6 carbon atoms.

<6> The sulfonate according to any one of <1> to <4>, wherein $A^+$ is a counter ion of the formula (IIb)

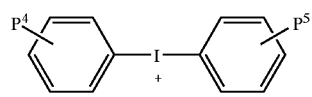

wherein $P^4$ and $P^5$ each independently represents a hydrogen, a hydroxyl, an alkyl having 1 to 6 carbon atoms or an alkoxy having 1 to 6 carbon atoms.

<7> The sulfonate according to any one of <1> to <4>, wherein $A^+$ is a counter ion of the formula (IIc)

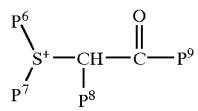

wherein $P^6$ and $P^7$ each independently represents an alkyl having 1 to 6 carbon atoms or a cycloalkyl having 3 to 10 carbon atoms, or $P^6$ and $P^7$ bond to form a divalent acyclic hydrocarbon having 3 to 7 carbon atoms which form a ring together with the adjacent $S^+$, and at least one —$CH_2$— in the divalent acyclic hydrocarbon may be substituted by —CO—, —O— or —S—; $P^8$ represents a hydrogen, $P^9$ represents an alkyl having 1 to 6 carbon atoms, a cycloalkyl having 3 to 10 carbon atoms or an aromatic ring group optionally substituted, or $P^8$ and $P^9$ bond to form 2-oxocycloalkyl together with the adjacent —CHCO—.

<8> The sulfonate according to any one of <1> to <4>, wherein $A^+$ is a counter ion of the formula (IId)

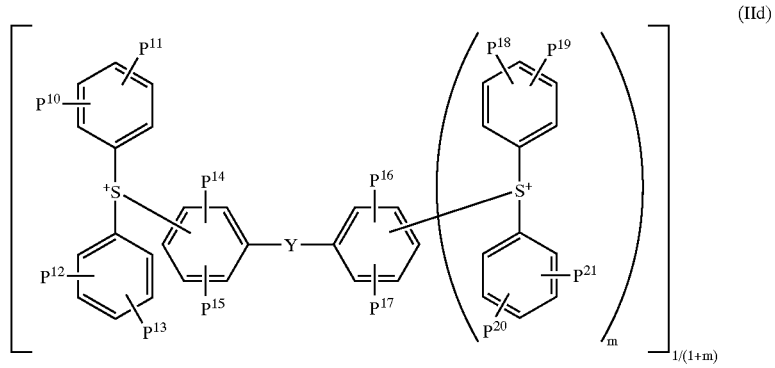

$P^{10}$, $P^{11}$, $P^{12}$, $P^{13}$, $P^{14}$, $P^{15}$, $P^{16}$, $P^{17}$, $P^{18}$, $P^{19}$, $P^{20}$, and $P^{21}$, each independently represents a hydrogen, a hydroxyl, an alkyl having 1 to 6 carbon atoms or an alkoxy having 1 to 6 carbon atoms, Y represents a sulfur or an oxygen, and m represents 0 or 1.

<9> A chemical amplification type positive resist composition comprising a sulfonate of the formula (I) and a resin which contains a structural unit having an acid labile group and which itself is insoluble or poorly soluble in an alkali aqueous solution but becomes soluble in an alkali aqueous solution by the action of an acid.

<10> The composition according to <9> wherein the content of the structural unit having an acid-labile group in all structural units of the resin is from 10 to 80% by mol, <11> The composition according to <9> or <10> wherein the structural unit having an acid-labile group is a structural unit derived from 2-alkyl-2-adamantyl (meth)acrylate or 1-(1-adamantyl)-1-alkylalkyl(meth)acrylate.

<12> The composition according to any one of <9> to <11> wherein the resin contains, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl (meth)acrylate, a structural unit derived from 3,5-dihydroxy-1-adamantyl (meth)acrylate, a structural unit derived from (meth)acryloyloxy-γ-butyrolactone having a lactone ring optionally substituted by alkyl, a structural unit of the formula (VIIa) and a structural unit of the formula (VIIb)

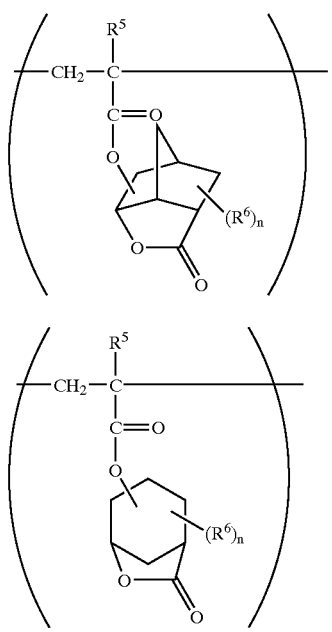

wherein $R^5$ represents a hydrogen, a methyl or a trifluoromethyl and $R^6$ represents a methyl or a trifluoromethyl, and n represents an integer of 0 to 3.

<13> The composition according to <9> or <10> wherein the resin further contains a structural unit derived from 2-norbornene and a structural unit derived from an aliphatic unsaturated dicarboxylic anhydride.

<14> The composition according to any one of <9> to <13> wherein the composition further comprises a basic nitrogen-containing organic compound as a quencher.

<15> The composition according to any one of <9> to <14> wherein the composition further comprises a surfactant.

<16> The composition according to any one of <9> to <15> wherein, in the formula (I), $A^+$ is a counter ion of the formula (IIa), the formula (IIb), the formula (IIc) or the formula (IId).

DESCRIPTION OF PREFERRED EMBODIMENTS

In the sulfonate of the formula (I), $Q^1$, $Q^2$, $Q^3$, $Q^4$ and $Q^5$ each independently represents a hydrogen; an alkyl having 1 to 16 carbon atoms; an alkoxy having 1 to 16 carbon atoms; a halogen; an aryl having 6 to 12 carbon atoms in which at least one hydrogen on the aryl may be substituted by an alkyl, a cycloalkyl, an alkoxy, a hydroxyl or a halogen; an arylalkyl having 7 to 12 carbon atoms in which at least one hydrogen on an aryl ring may be substituted by an alkyl, a cycloalkyl, an alkoxy, a hydroxyl or a halogen; a cyano; a mercapto; an alkylthio having 1 to 16 carbon atoms; a hydroxyl; a nitro or a group of the formula (I'); with the proviso that at least one of $Q^1$, $Q^2$, $Q^3$, $Q^4$ and $Q^5$ is a group of the formula (II).

The alkyl having 1 to 16 carbon atoms in $Q^1$, $Q^2$, $Q^3$, $Q^4$ or $Q^5$ may be straight chained or branched and examples thereof include methyl, ethyl, propyl, isopropyl, butyl, tert-butyl, pentyl, hexyl, octyl, decyl, dodecyl, hexadecyl, and the like.

The alkoxy having 1 to 16 carbon atoms in $Q^1$, $Q^2$, $Q^3$, $Q^4$ or $Q^5$ may be straight chained or branched and examples thereof include methoxy, ethoxy, propoxy, isopropoxy, butoxy, tert-butoxy, pentyloxy, hexyloxy, isopentyloxy, decyloxy, dodecyloxy, hexadecyloxy, and the like.

Examples of the unsubstituted or substituted aryl having 6 to 12 carbon atoms in $Q^1$, $Q^2$, $Q^3$, $Q^4$ or $Q^5$ include phenyl, tolyl, methoxyphenyl, naphtyl and the like.

Examples of the unsubstituted or substituted arylalkyl having 7 to 12 carbon atoms in $Q^1$, $Q^2$, $Q^3$, $Q^4$ or $Q^5$ include benzyl, chloromethoxyphenylethyl, methoxybenzyl, and the like.

Examples of halogen in $Q^1$, $Q^2$, $Q^3$, $Q^4$ or $Q^5$ include fluorine, chlorine, bromine, iodine, and the like.

The alkylthio having 1 to 16 carbon atoms in $Q^1$, $Q^2$, $Q^3$, $Q^4$ or $Q^5$ may be straight chained or branched and examples thereof include methylthio, ethylthio, propylthio, isopropylthio, butylthio, tert-butylthio, pentylthio, hexylthio, octylthio, decylthio, dodecylthio, hexadecylthio, and the like.

In the formula (I'), R represents an aryl having 6 to 12 carbon atoms, a group of the formula (II') or a group of the formula (II").

Examples of the aryl having 6 to 12 carbon atoms in R include phenyl, tolyl, methoxyphenyl, naphtyl and the like.

In the formula (II'), $R^1$ and $R^2$ each independently represents an alkyl having 1 to 12 carbon atoms, a cycloalkyl having 3 to 12 carbon atoms, an arylalkyl having 7 to 12 carbon atoms or an aryl having 6 to 12 carbon atoms, and at least one hydrogen on an aryl ring in the arylalkyl or in the aryl may be substituted by an alkyl, a cycloalkyl, an alkoxy, a hydroxyl or a halogen, or $R^1$ and $R^2$ bond to form a monocyclic or polycyclic hydrocarbon group together with adjacent —C($R^a$)—, $R^a$ represents an alkyl having 1 to 8 carbon atoms, and —CH$_2$— in the alkyl except the one at the terminal position may be substituted by —CO—, —O— or —S—.

In the formula (II''), R$^3$ and R$^4$ each independently represents a hydrogen, an alkyl having 1 to 12 carbon atoms, a cycloalkyl having 3 to 12 carbon atoms, an arylalkyl having 7 to 12 carbon atoms or an aryl having 6 to 12 carbon atoms, and at least one hydrogen on an aryl ring in the arylalkyl or in the aryl may be substituted by an alkyl, a cycloalkyl, an alkoxy, a hydroxyl or a halogen, or R$^3$ and R$^4$ bond to form a monocyclic or polycyclic hydrocarbon group together with adjacent —CH—.

The alkyl having 1 to 12 carbon atoms in R$^1$, R$^2$, R$^3$ or R$^4$ may be straight chained or branched and examples thereof include methyl, ethyl, propyl, isopropyl, butyl, tert-butyl, pentyl, hexyl, octyl, decyl, dodecyl, and the like.

Examples of the cycloalkyl having 3 to 12 carbon atoms in R$^1$, R$^2$, R$^3$ or R$^4$ include cyclopropyl, cyclobutyl, cyclopentyl, cyclohexyl, and the like.

Examples of the unsubstituted or substituted arylalkyl having 7 to 12 carbon atoms in R$^1$, R$^2$, R$^3$ or R$^4$ include benzyl, chloromethoxyphenylethyl, methoxybenzyl, and the like.

Examples of the unsubstituted or substituted aryl having 6 to 12 carbon atoms in R$^1$, R$^2$, R$^3$ or R$^4$ include phenyl, tolyl, methoxyphenyl, naphtyl and the like.

Examples of the unsubstituted or substituted alkyl having 1 to 8 carbon atoms in R$^a$ include as follows:

—CH$_3$ (a-1)

—CH$_2$CH$_3$ (a-2)

—CH$_2$CH$_2$CH$_3$ (a-3)

—CH$_2$CH$_2$CH$_2$CH$_3$ (a-4)

—CH$_2$CH$_2$CH$_2$CH$_2$CH$_2$CH$_2$CH$_2$CH$_3$ (a-5)

—CH$_2$OCH$_3$ (a-6)

—CH$_2$OCH$_2$CH$_2$CH$_3$ (a-7)

—CH$_2$CH$_2$OCH$_2$CH$_3$ (a-8)

—CH$_2$SCH$_3$ (a-9)

—CH$_2$SCH$_2$CH$_2$CH$_3$ (a-10)

—CH$_2$COCH$_3$ (a-11)

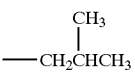
(a-12)

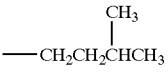
(a-13)

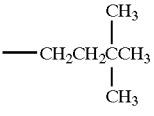
(a-14)

Methyl and ethyl are preferred for R$^a$.

Examples of the monocyclic or polycyclic hydrocarbon group formed by R$^1$ and R$^2$ together with the adjacent —C(R$^a$)— or formed by R$^3$ and R$^4$ together with the adjacent —CH— include R$^a$ substituted or unsubstituted cyclopentyl, R$^a$ substituted or unsubstituted cyclohexyl, R$^a$ substituted or unsubstituted cyclooctyl, R$^a$ substituted or unsubstituted adamantyl, R$^a$ substituted or unsubstituted norbornyl, and the like.

Specific examples of the formula (II') include t-butyl, 1,1-dimethylpropyl, 1-methyl-1-phenylethyl, 1-methyl-1-phenylpropyl, 1,1-diphenylethyl, 1,1-dimethyl-2-phenylethyl, 1,1-dimethyl-3-phenylpropyl, 1-methyl-1,3-diphenylpropyl, 1-methylcyclopentyl, 1-ethylcyclopentyl, 1-methylcyclohexyl, 1-ethylcyclohexyl, 1-methylcyclooctyl, 1-ethylcyclooctyl, 2-methyl-2-adamantyl, 2-ethyl-2-adamantyl, 2-methyl-2-norbornyl, 2-ethyl-2-norbornyl, 2-isopropyl-2-adamantyl, and the like. Specific examples of the formula (II'') include 1-methylethyl, 1-ethylpropyl, 1-phenylethyl, 1-phenylpropyl, 1-methyl-2-phenylethyl, 1-methyl-3-phenylpropyl, 1,3-diphenylpropyl, 1-methyl-1-cyclohexylmethyl, 1-phenyl-cyclohexylmethyl, 1-cyclohexyl-3-phenylpropyl, cyclopentyl, cyclohexyl, cyclooctyl, 2-adamantyl, 2-norbornyl, and the like.

In the sulfonate of the formula (I), at least one of Q$^1$, Q$^2$, Q$^3$, Q$^4$ and Q$^5$ is a group of the formula (II).

Preferred examples of the formula (II) include 2-methyl-2-adamantyloxycarbonyl and 2-ethyl-2-adamantyloxycarbonyl.

Specific examples of the sulfonate ion in the sulfonate of the formula (I) include the followings:

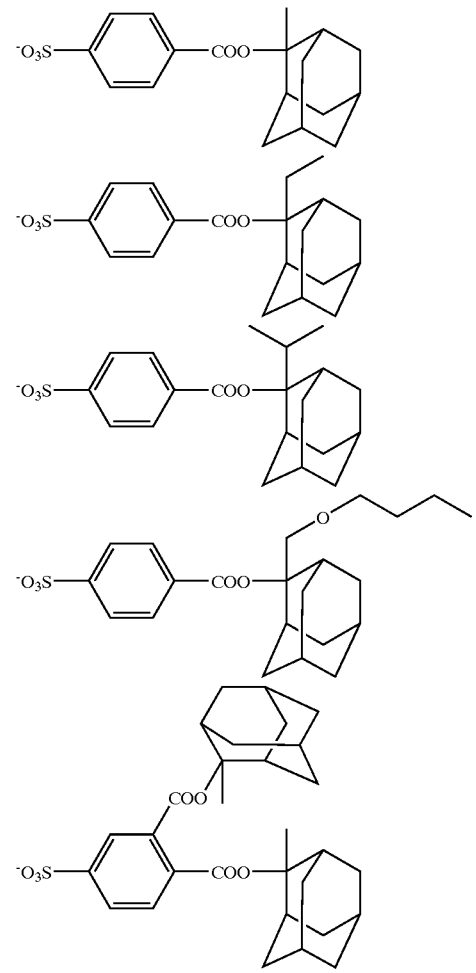

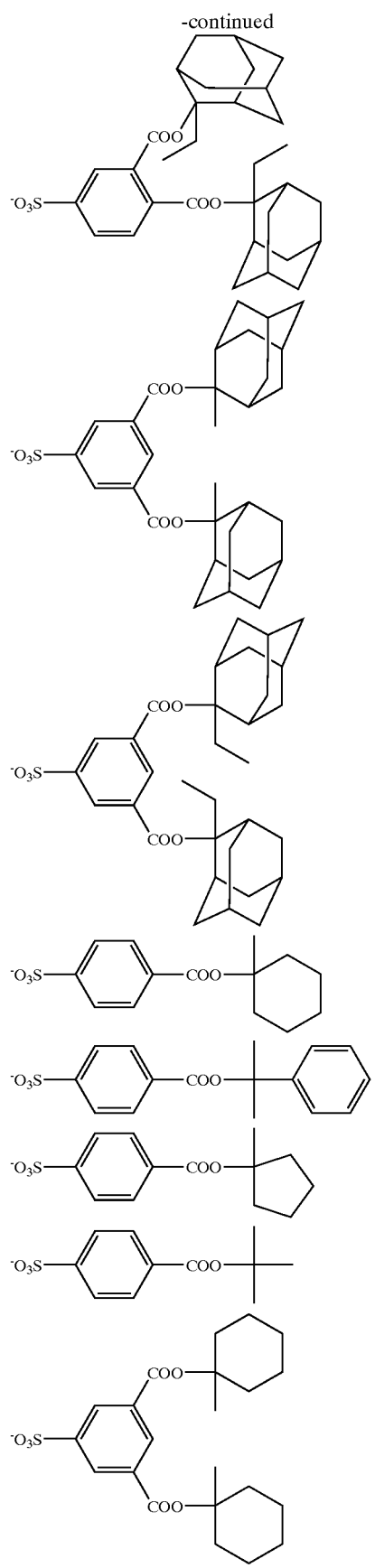
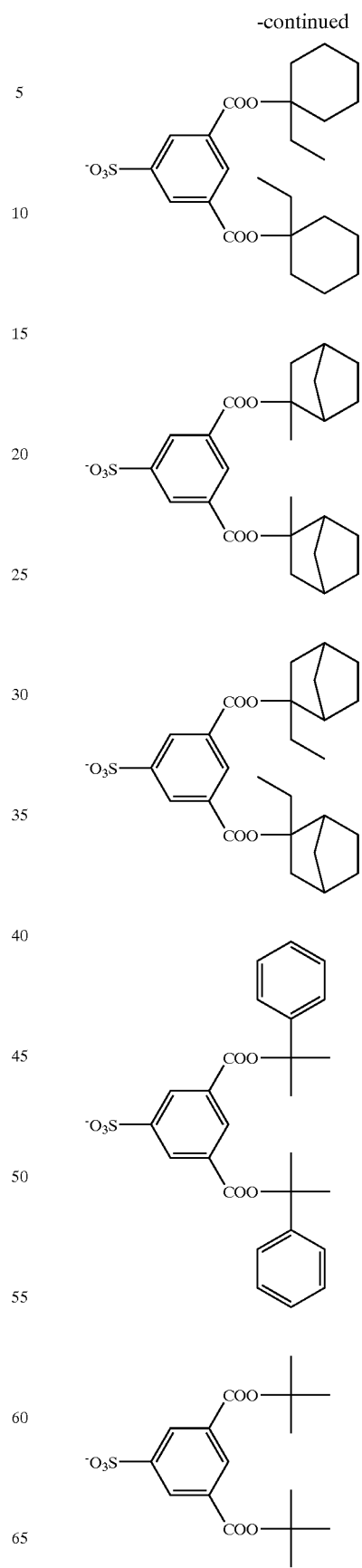

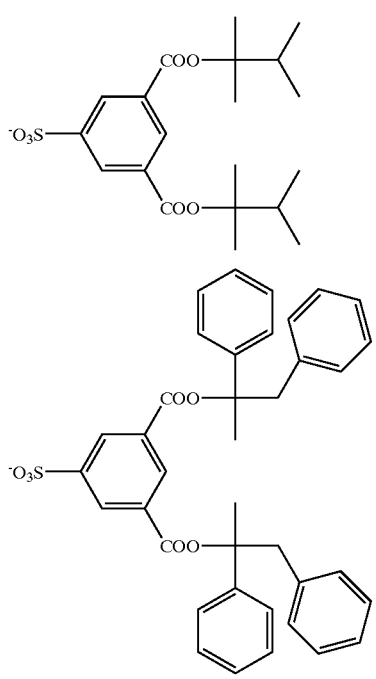

In the sulfonate of the formula (I), A$^+$ represents a counter ion and as the counter ion, a counter ions of the following formula (IIa), (IIb), (IIc) and (IId) are preferable:

A counter ion of the formula (IIa)

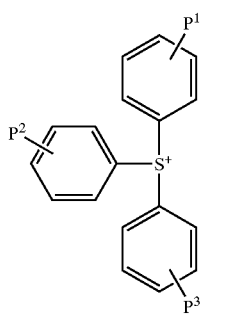

(IIa)

wherein $P^1$, $P^2$ and $P^3$ each independently represents a hydrogen, a hydroxyl, an alkyl having 1 to 6 carbon atoms or an alkoxy having 1 to 6 carbon atoms.

A counter ion of the formula (IIb)

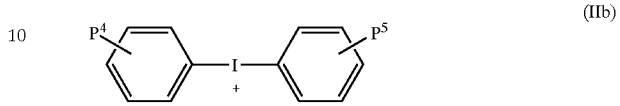

(IIb)

wherein $P^4$ and $P^5$ each independently represents a hydrogen, a hydroxyl, an alkyl having 1 to 6 carbon atoms or an alkoxy having 1 to 6 carbon atoms.

A counter ion of the formula (IIc):

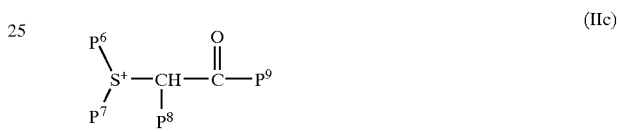

(IIc)

wherein $P^6$ and $P^7$ each independently represents an alkyl having 1 to 6 carbon atoms or a cycloalkyl having 3 to 10 carbon atoms, or $P^6$ and $P^7$ bond to form a divalent acyclic hydrocarbon having 3 to 7 carbon atoms which form a ring together with the adjacent S$^+$, and at least one —CH$_2$— in the divalent acyclic hydrocarbon may be substituted by —CO—, —O— or —S—; $P^8$ represents a hydrogen, $P^9$ represents an alkyl having 1 to 6 carbon atoms, a cycloalkyl having 3 to 10 carbon atoms or an aromatic ring group optionally substituted, or $P^8$ and $P^9$ bond to form 2-oxocycloalkyl together with the adjacent —CHCO—.

A counter ion of the formula (IId):

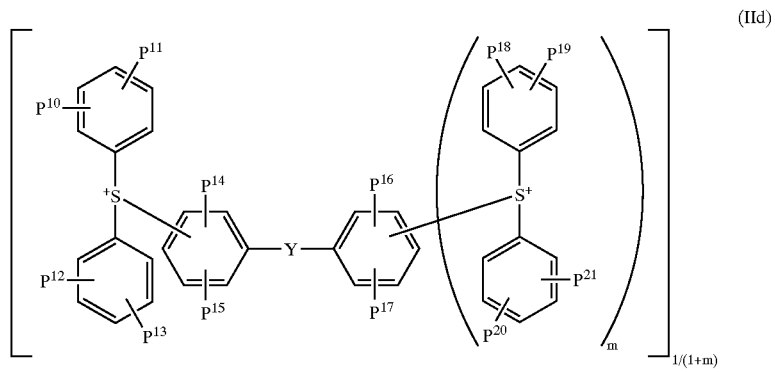

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represents a hydrogen, a hydroxyl, an alkyl having 1 to 6 carbon atoms or an alkoxy having 1 to 6 carbon atoms, Y represents a sulfur or an oxygen, and m represents 0 or 1.

In the formula (IIa), $P^1$, $P^2$ and $P^3$ each independently represents a hydrogen, a hydroxyl, an alkyl having 1 to 6 carbon atoms or an alkoxy having 1 to 6 carbon atoms, and the alkyl and alkoxy may be linear or branched in the case of 3 or more carbon atoms.

In the formula (IIb), $P^4$ and $P^5$ each independently represents a hydrogen, a hydroxyl, an alkyl having 1 to 6 carbon atoms or an alkoxy having 1 to 6 carbon atoms, and the alkyl and alkoxy may be linear or branched in the case of 3 or more carbon atoms.

In $P^1$, $P^2$, $P^3$, $P^4$ and $P^5$, specific examples of the alkyl include methyl, ethyl, propyl, isopropyl, butyl, tert-butyl, pentyl, hexyl and the like, and examples of the alkoxy include methoxy, ethoxy, propoxy, butoxy and the like.

In the formula (IIc), $P^6$ and $P^7$ each independently represents an alkyl having 1 to 6 carbon atoms or a cycloalkyl having 3 to 10 carbon atoms, or $P^6$ and $P^7$ bond to form a divalent acyclic hydrocarbon having 3 to 7 carbon atoms which form a ring together with the adjacent $S^+$, At least one —CH$_2$— in the divalent acyclic hydrocarbon may be substituted by —CO—, —O— or —S—.

$P^8$ represents a hydrogen and $P^9$ represents an alkyl having 1 to 6 carbon atoms, a cycloalkyl having 3 to 10 carbon atoms or an aromatic ring group optionally substituted, or $P^8$ and $P^9$ bond to form 2-oxocycloalkyl together with the adjacent —CHCO—.

In $P^6$, $P^7$ and $P^9$, specific examples of the alkyl include methyl, ethyl, propyl, isopropyl, butyl, tert-butyl, pentyl, hexyl and the like, and specific examples of the cycloalkyl include cyclopropyl, cyclobutyl, cyclopentyl, cyclohexyl, cycloheptyl and the like. Specific examples of the ring group formed by adjacent $S^+$ and divalent acyclic hydrocarbon by $P^6$ and $P^7$ include pentamethylenesulfonio group, tetramethylenesulfonio group, oxybisethylenesulfonio group, and the like. In $P^9$, specific examples of the aromatic ring group include phenyl, tolyl, xylyl, naphtyl and the like. Specific examples of the 2-oxocycloalkyl formed by bonding $P^8$ and $P^9$ together with the adjacent —CHCO— include 2-oxocyclohexyl, 2-oxocyclopentyl and the like.

In the formula (IId), $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen, a hydroxyl, an alkyl having 1 to 6 carbon atoms or an alkoxy having 1 to 6 carbon atoms. The alkyl and alkoxy may be linear or branched in the case of 3 or more carbon atoms. Specific examples of the alkyl include methyl, ethyl, propyl, isopropyl, butyl, tert-butyl, pentyl, hexyl and the like, and examples of the alkoxy include methoxy, ethoxy, propoxy, butoxy and the like. Y represents a sulfur or an oxygen. m represents 0 or 1.

Preferred examples of the sulfonate of the formula (I) include sulfonates of the following formulae (III), (IV), (V) and (VI):

The sulfonate of the formula (III)

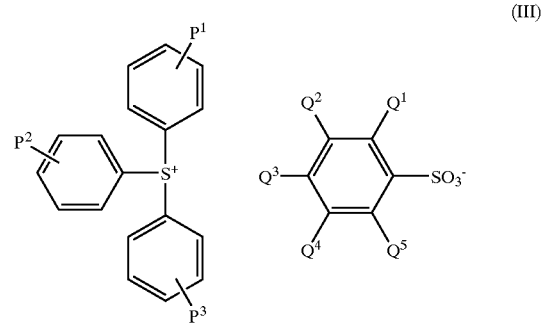

wherein $Q^1$, $Q^2$, $Q^3$, $Q^4$, $Q^5$, $P^1$, $P^2$ and $P^3$ are as defined above.

The sulfonate of the formula (IV)

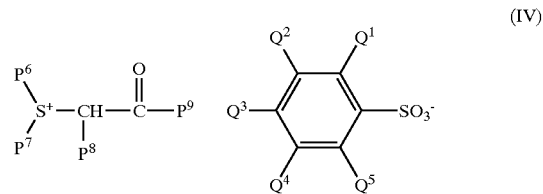

wherein $Q^1$, $Q^2$, $Q^3$, $Q^4$, $Q^5$, $P^6$, $P^7$, $P^8$ and $P^9$ are as defined above.

The sulfonate of the formula (V)

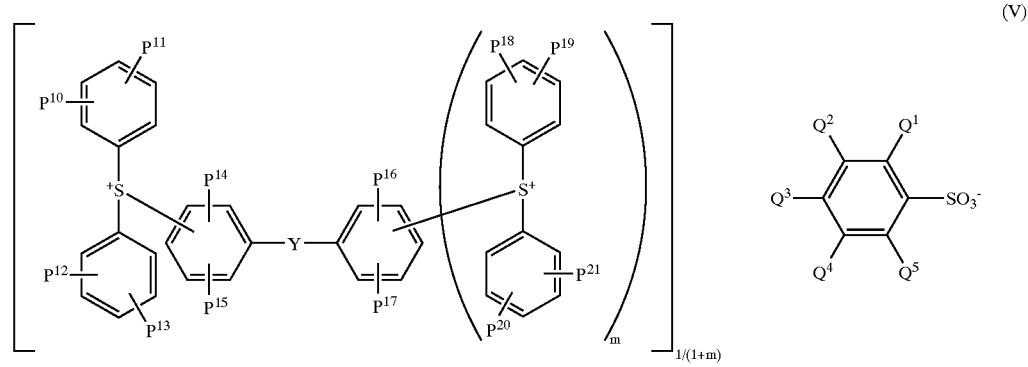

wherein $Q^1$, $Q^2$, $Q^3$, $Q^4$, $Q^5$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, Y and m are as defined above.
The sulfonate of the formula (VI)
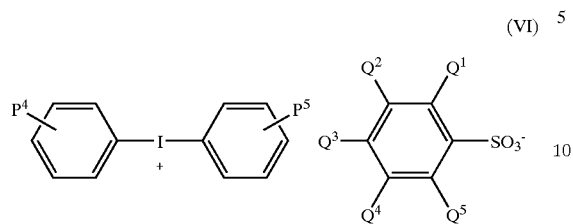
(VI)
wherein $Q^1$, $Q^2$, $Q^3$, $Q^4$, $Q^5$, $P^4$ and $P^5$ are as defined above.
Specific examples of the counter ion represented by $A^+$ in the sulfonate of the formula (I) include the followings:
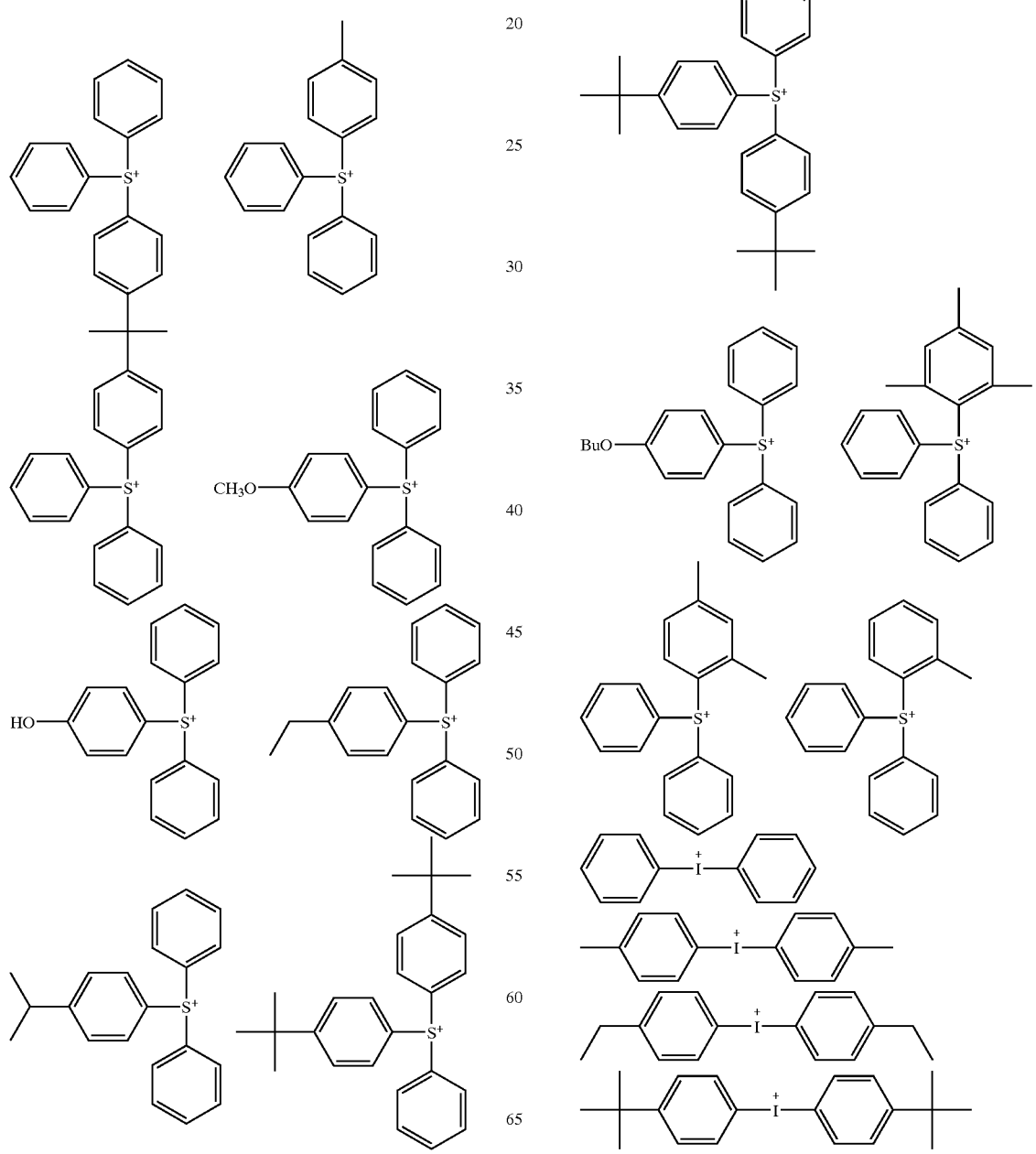
-continued

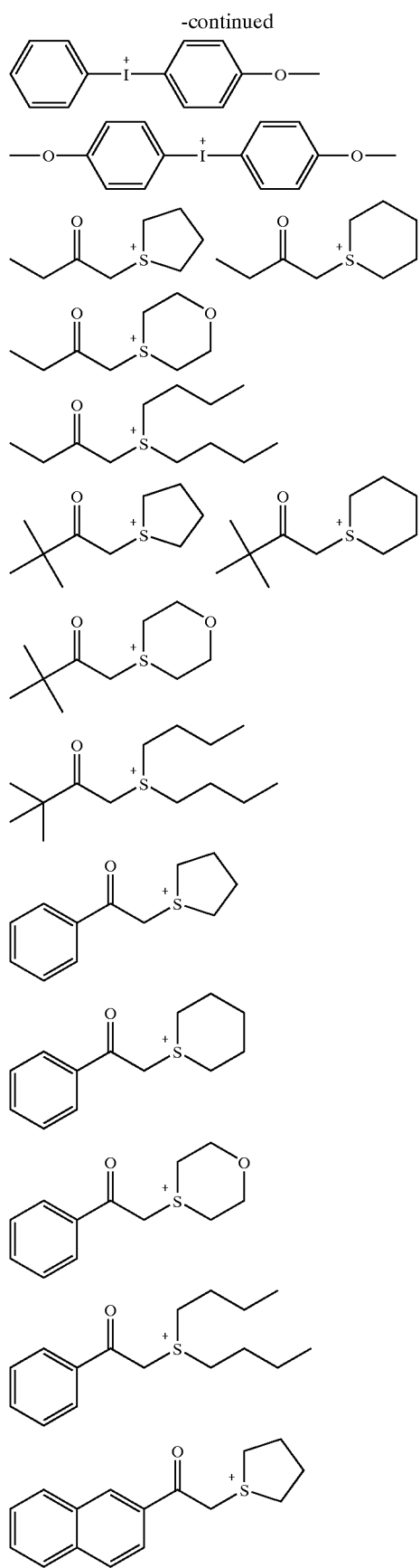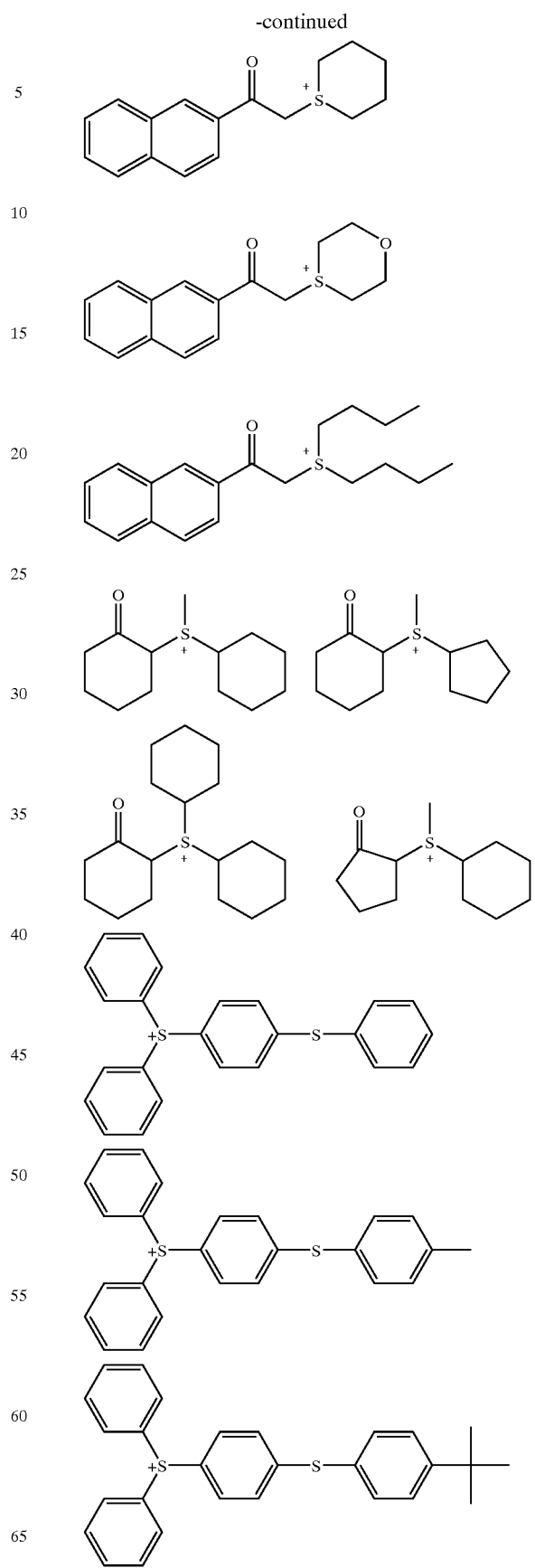

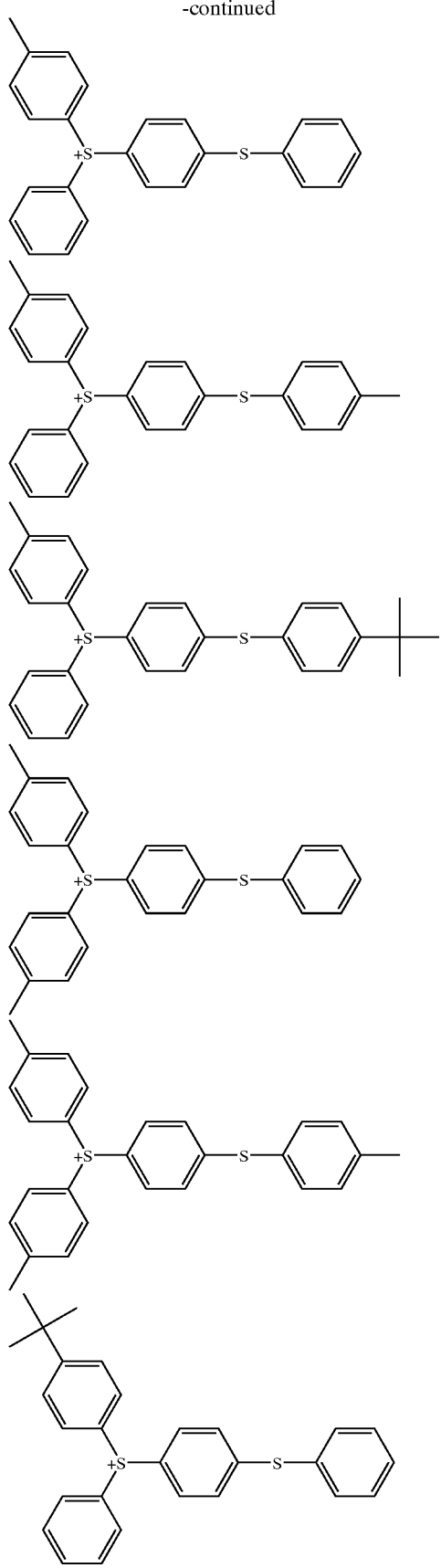
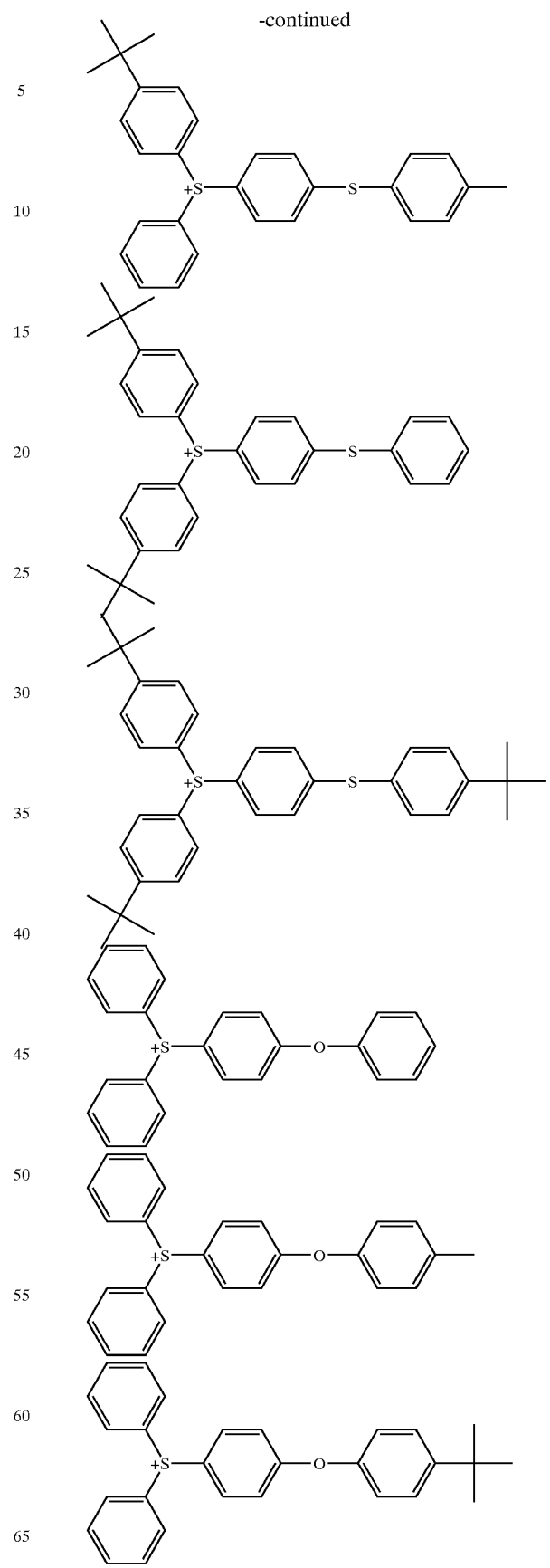

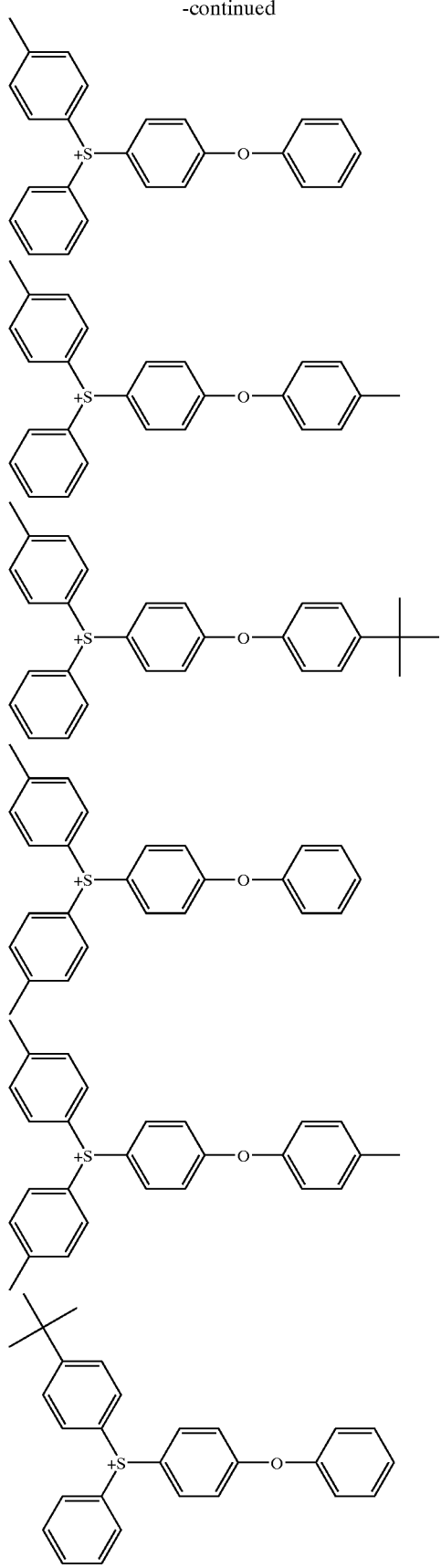
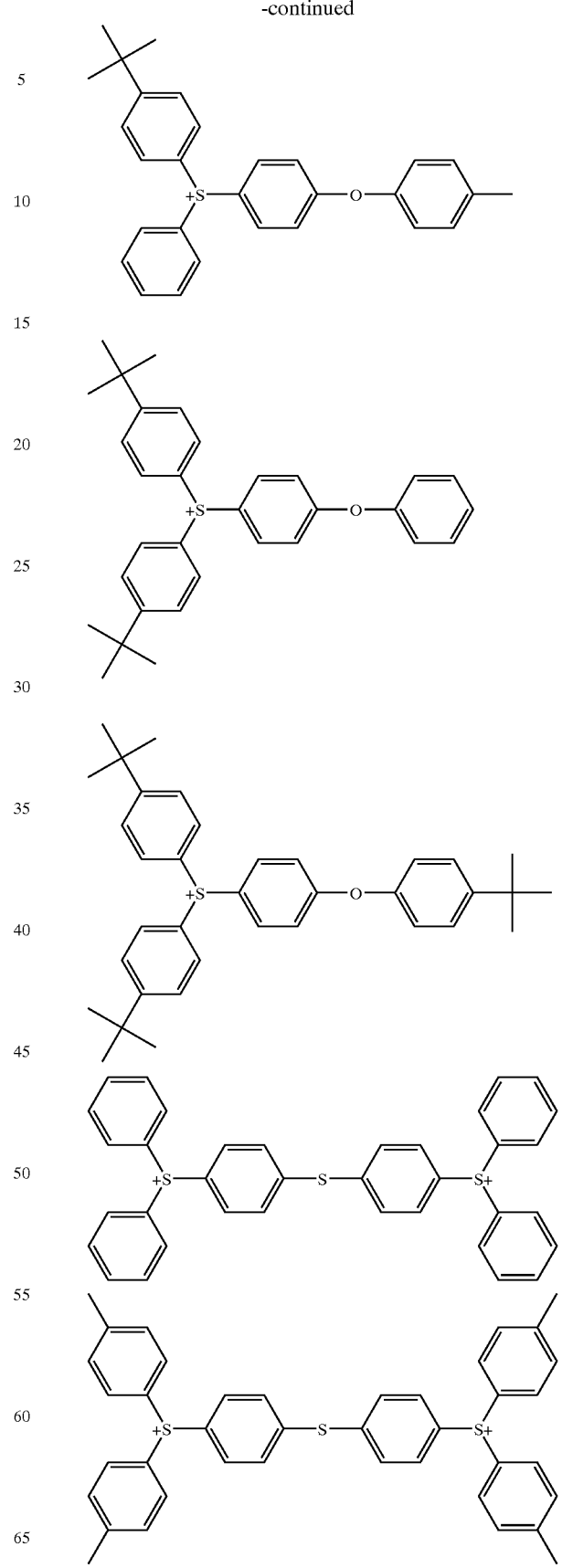

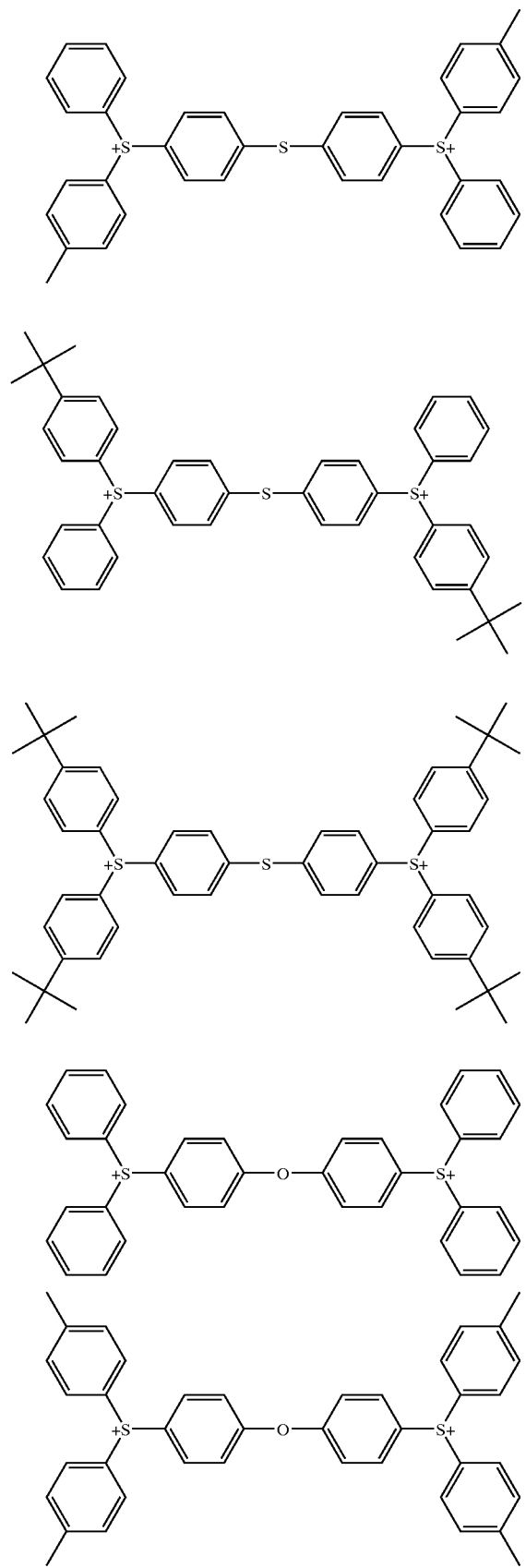

The sulfonates of the formulae (III), (IV), (V) and (VI) can be produced according to conventional methods as shown below.

The sulfonate of the formula (III) can be produced, for example, by a method reacting corresponding triphenylsulfonium bromide with silver salt of sulfonic acid having the same structure of anion part of the intended sulfonate; a method reacting corresponding aryl Grignard reagent with thionyl chloride, reacting the product with triorganosilyl halide to obtain triarylsulfonium halide, and then reacting the triarylsulfonium halide with silver salt of sulfonic acid having the same structure of anion part of the intended sulfonate according to the method described in JP-H08-311018-A; and the like. The sulfonate in which $P^1$, $P^2$ or $P^3$ in the formula (III) is hydroxy, can be produced by reacting triphenylsulfonium salt having tert-butoxy on its benzene ring with sulfonic acid having the same structure of anion part of the intended sulfonate according to the method described in JP-H08-157451-A.

The sulfonate of the formula (IV) can be produced, for example, by a method reacting corresponding β-haloketone with corresponding sulfide compound to obtain corresponding sulfonium halide, and then reacting the corresponding sulfonium halide and corresponding sulfonic acid or metal salt thereof having the same structure of anion part of the intended sulfonate applying the method described in J. Polymer Science, Polymer Chemistry Edition, Vol. 17, 2877–2892 (1979) written by J. V. Crivello et al.

The sulfonate of the formula (V) can be produced, for example, by a method reacting corresponding sulfonium halide with sulfonic acid or metal salt thereof having the same structure of anion part of the intended sulfonate; a method reacting corresponding diphenylsulfoxide, aryl compound (i.e. diphenyl ether, diphenylsufoxide, and the like) and perfluoroalkanesulfonic acid in the presence of trifluoroacetic anhydride to obtain corresponding sulfonium salt, converting the corresponding sulfonium salt to salt of corresponding sulfonium cation and hydroxy anion, then salt-exchanging, the product with halogenide (i.e. ammonium iodide, potassium iodide and the like) to obtain salt of corresponding sulfonium cation and halogen anion, and thereafter, reacting the salt with corresponding sulfonic acid having the same structure of anion part of the intended sulfonate according to the method described in Chem. Pharm. Bull., Vol. 29, 3753 (1981).

The sulfonate of the formula (VI) can be produced, for example, by a method reacting iodosyl sulfate with corresponding aryl compound, and then adding thereto corresponding sulfonic acid having the same structure of anion part of the intended sulfonate according to a method described in J. Am. Chem. Soc., vol. 81, 342 (1959); a method adding iodine and trifluoroacetic acid to a mixture of acetic anhydride and fuming nitric acid, then reacting the reaction mixture and corresponding aryl compound, and then adding thereto corresponding sulfonic acid having the same structure of anion part of the intended sulfonate; a method reacting a mixture of corresponding aryl compound, acetic anhydride and potassium iodate by adding drop-wise concentrated sulfuric acid thereto, and then adding thereto corresponding sulfonic acid having the same structure of anion part of the intended sulfonate according to a method described in JP-H09–179302-A; and the like.

Next, resin components constituting the present composition will be explained. The resin used in the present composition contains a structural unit having an acid-labile group and the resin is insoluble or poorly soluble itself in alkali aqueous solution and shows partial dissociation of groups by the action of an acid to become soluble in alkali aqueous solution after the dissociation. The acid-labile group can be selected from conventionally known various groups.

Specifically, various carboxylate groups (—COOR) are mentioned as the acid-labile group, and examples thereof include alky carboxylate groups such as methyl carboxylate group and tert-butyl carboxylate group; acetal type carboxylate groups such as methoxymethyl carboxylate group, ethoxymethyl carboxylate group, 1-ethoxyethyl carboxylate group, 1-isobutoxyethyl carboxylate group, 1-isopropoxyethyl carboxylate group, 1-ethoxypropyl carboxylate group, 1-(2-methoxyethoxy)ethyl carboxylate group, 1-(2-acetoxyethoxy)ethyl carboxylate group, 1-[2-(1-adamantyloxy)ethoxy]ethyl carboxylate group, 1-[2-(1-adamantanecarbonyloxy)ethoxy]ethyl carboxylate group, tetrahydro-2-furyl carboxylate group and tetrahydro-2-pyranyl carboxylate group; alicyclic ester groups such as isobornyl carboxylate group, 2-alkyl-2-adamantyl carboxylate group, 1-(1-adamantyl)-1-alkylalkyl carboxylate group, and the like.

Monomers to be derived into structural units having such carboxylate group (—COOR) may be (meth)acryl-based monomers such as methacrylates and acrylates, or those obtained by bonding of a carboxylate group to alicyclic compound such as norbornenecarboxylate, tricyclodecenecarboxylate and tetracyclodecenecarboxylate.

Among the above-mentioned monomers, it is preferable to use those having a bulky group containing alicyclic group such as, for example, 2-alkyl-2-adamantyl and 1-(1-adamantyl)-1-alkylalkyl, as the group dissociated by the action of an acid, since excellent resolution is obtained when used in the present composition.

Examples of such monomer containing a bulky group include 2-alkyl-2-adamantyl(meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, 1-(1-adamantyl)-1-alkylalkyl α-chloroacrylate and the like.

Particularly when 2-alkyl-2-adamantyl(meth)acrylate or 2-alkyl-2-adamantyl α-chloroacrylate is used as the monomer for the resin component in the present composition, excellent resolution is obtained. Typical examples of such 2-alkyl-2-adamantyl(meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate and the like. When particularly 2-ethyl-2-adamantyl(meth)acrylate or 2-ethyl-2-adamantyl α-chloroacrylate is used for the present composition, balance between sensitivity and heat resistance is excellent. In the present invention, two or more kind of monomers having group dissociated by the action of an acid may be used together, if necessary.

2-Alkyl-2-adamantyl(meth)acrylate can usually be produced by reacting 2-alkyl-2-adamantanol or metal salt thereof with an acrylic halide or methacrylic halide. 2-Alkyl-2-adamantyl α-chloroacrylate can usually be produced by reacting 2-alkyl-2-adamantanol or metal salt thereof with an α-chloroacrylic halide.

The resin used for the present composition can also contain, in addition to the above-mentioned structural units having an acid-labile group, other structural units not dissociated or not easily dissociated by the action of an acid. Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural unit derived from 2-norbornene, structural unit derived from (meth)acrylonitrile, and the like.

In the case of KrF exposure, there is no problem on light absorption, and a structural unit derived from hydroxystyrene can be further contained.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl, a structural unit of the following formula (VIIa) and a structural unit of the following formula (VIIb), in the resin in the present composition, is preferable from the standpoint of the adhesiveness of resist to a substrate.

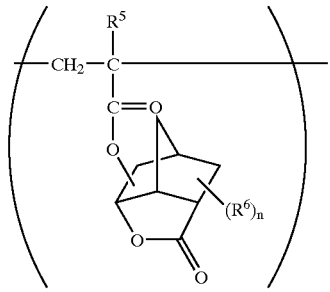

(VIIa)

(VIIb)

In the formulae (VIIa) and (VIIb), $R^5$ represents a hydrogen, a methyl or a trifluoromethyl and $R^6$ represents a methyl or a trifluoromethyl, and n represents an integer of 0 to 3. When n represents 2 or 3, each of the $R^6$ may be same or different.

3-Hydroxy-1-adamantyl(meth)acrylate and 3,5-dihydroxy-1-adamantyl(meth)acrylate can be produced, for example, by reacting corresponding hydroxyadamantane with (meth)acrylic acid or its acid halide, and they are also commercially available.

Further, (meth)acryloyloxy-γ-butyrolactone having a lactone ring optionally substituted by alkyl can be produced by reacting corresponding α- or β-bromo-γ-butyrolactone with acrylic acid or methacrylic acid, or reacting corresponding α- or β-hydroxy-γ-butyrolactone with acrylic halide or methacrylic halide.

As monomers to be derived into structural units of the formulae (VIIa) and (VIIb), specifically listed are, for example, (meth)acrylates of alicyclic lactones having hydroxyl described below, and mixtures thereof, and the like. These esters can be produced, for example, by reacting corresponding alicyclic lactone having hydroxyl with (meth)acrylic acids, and the production method thereof is described in, for example, JP2000-26446-A.

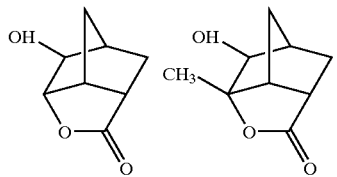

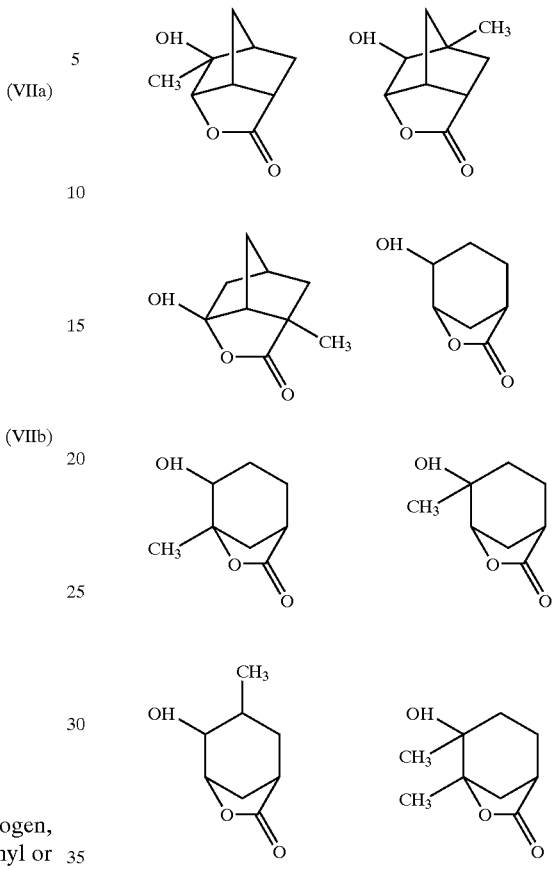

When any of the structural unit derived from 3-hydroxy-1-adamantyl (meth)acrylate, the structural unit derived from 3,5-dihydroxy-1-adamantyl (meth)acrylate, the structural unit derived from α- or β-(meth)acryloyloxy-γ-butyrolactone having a lactone ring optionally substituted by alkyl, and the structural unit of the formulae (VIIa) and (VIIb) is contained in the resin, not only the adhesiveness of the resist to a substrate is improved, but also the resolution of the resist is improved.

Here, examples of the (meth)acryloyloxy-γ-butyrolactone having a lactone ring optionally substituted by alkyl include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF lithography and electron beam lithography, using a structure unit derived from hydroxystyrene as one of the resin components is preferred. Specifically, copolymerization resins containing a structural unit derived from p- or m-hydroxystyrene as described below are listed. For obtaining such copolymerization resins, the corresponding (meth)acrylic ester monomer can be radical-polymerized with acetoxystyrene and styrene, and then the acetoxy group in the structure unit derived from acetoxystyrene can be de-acetylated with an acid.

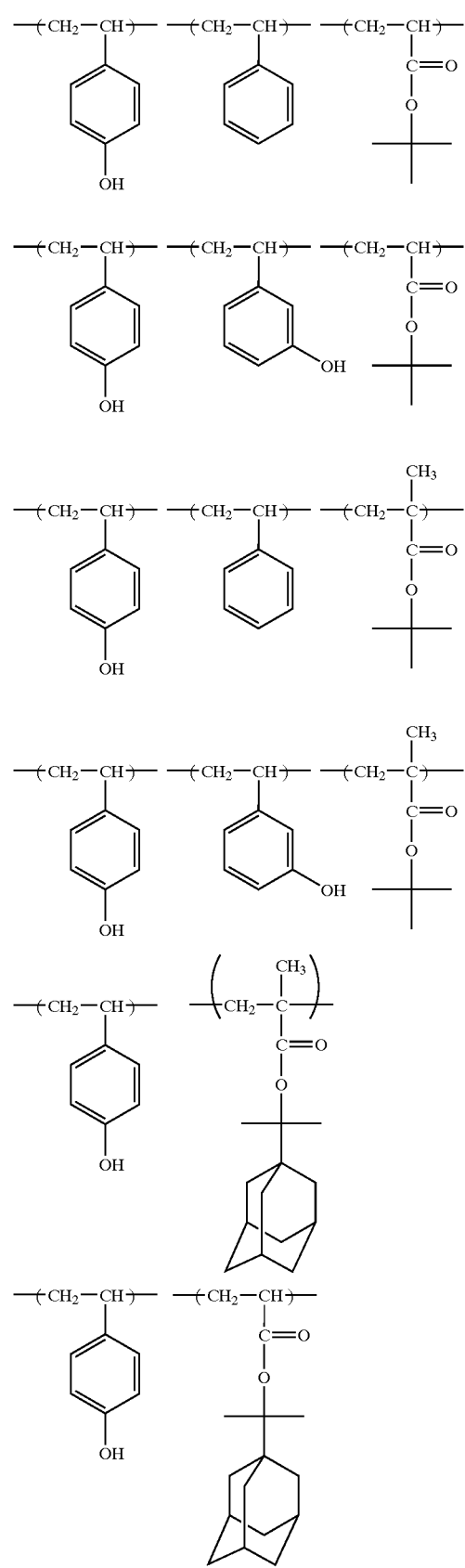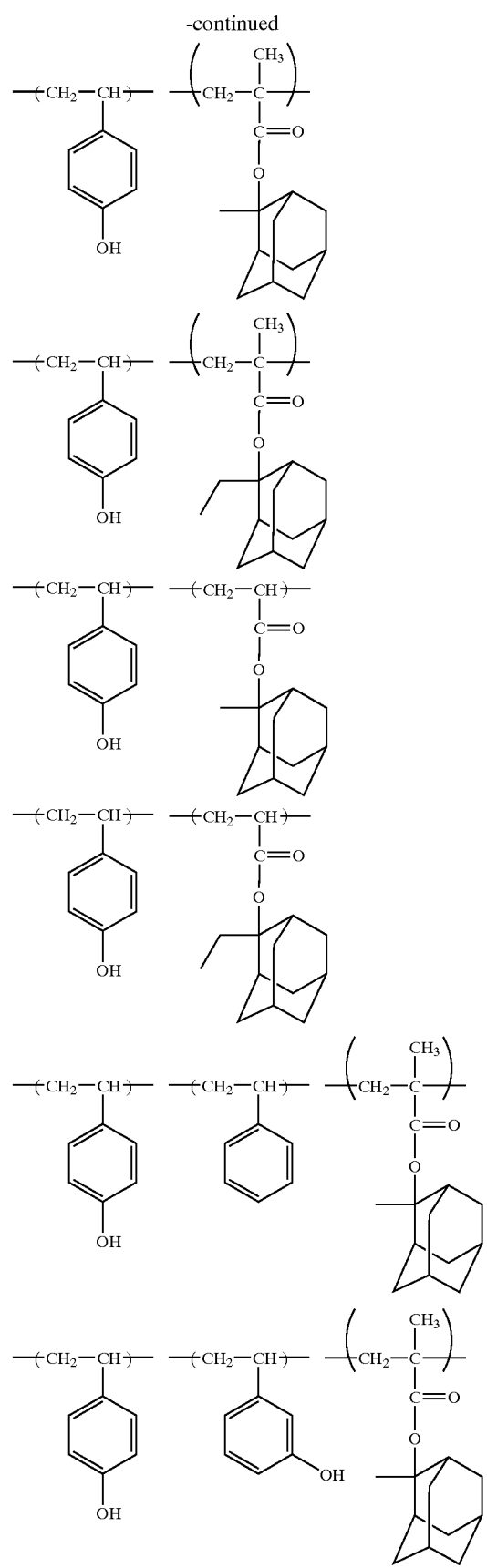
-continued

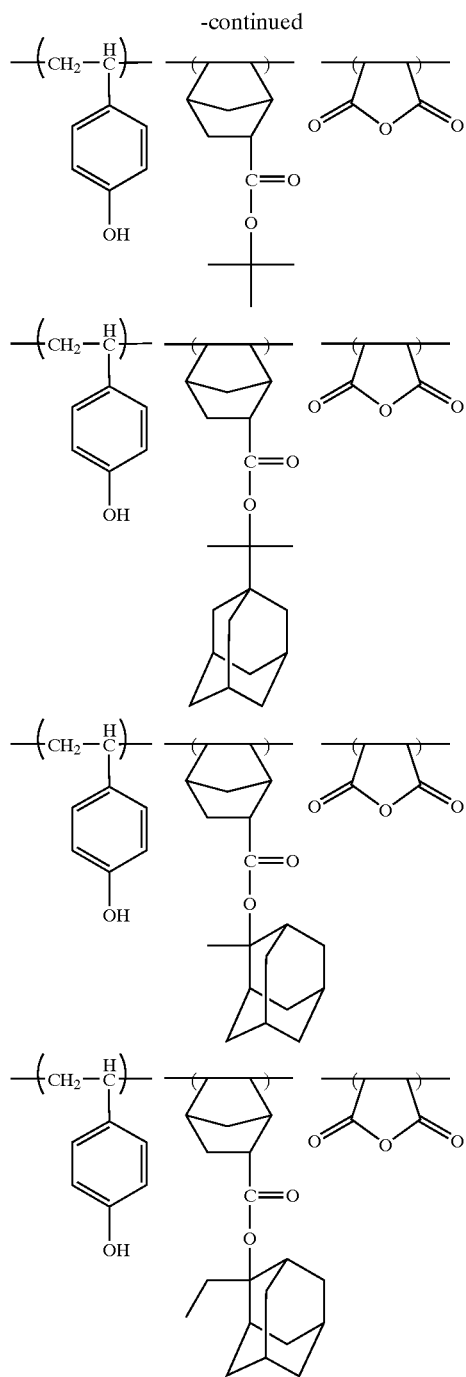

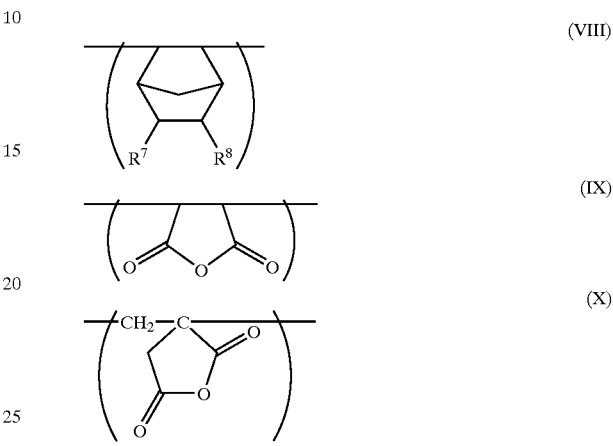

2-norbornene is formed by opening of its double bond, and can be represented by the formula (VIII). The structural unit derived from maleic anhydride and the structural unit derived from itaconic anhydride which are the structural unit derived from aliphatic unsaturated dicarboxylic anhydrides are formed by opening of their double bonds, and can be represented by the formula (IX) and the formula (X), respectively.

Here, $R^7$ and $R^8$ in the formula (VIII) each independently represent hydrogen, alkyl having 1 to 3 carbon atoms, hydroxyalkyl having 1 to 3 carbon atoms, carboxyl, cyano or —COOZ group in which Z represents alcohol residue, or $R^7$ and $R^8$ can bond together to form a carboxylic anhydride residue represented by —C(=O)OC(=O)—.

In $R^7$ and $R^8$, examples of the alkyl include methyl, ethyl, propyl and isopropyl, specific examples of hydroxyalkyl include hydroxymethyl, 2-hydroxyethyl and the like.

In $R^7$ and $R^8$, —COOZ group is an ester formed from carboxyl, and as the alcohol residue corresponding to Z, for example, optionally substituted alkyls having about 1 to 8 carbon atoms, 2-oxooxolan-3- or -4-yl and the like are listed, and as the substituent on the alkyl, hydroxyl, alicyclic hydrocarbon residues and the like are listed.

Specific examples of —COOZ include methoxycarbonyl, ethoxycarbonyl, 2-hydroxyethoxycarbonyl, tert-butoxycarbony, 2-oxooxalan-3-yloxycarbonyl, 2-oxooxalan-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl, 1-(1-adamantyl)-1-methylethoxycarbonyl and the like.

Specific examples of the monomer used to derive the structural unit represented by the formula (VIII) may include the followings;

2-norbornene,
2-hydroxy-5-norbornene,
5-norbornen-2-carboxylic acid,
methyl 5-norbornen-2-carboxylate,
t-butyl 5-norbornen-2-carboxylate,
1-cyclohexyl-1-methyl ethyl 5-norbornen-2-carboxylate,
1-(4-methylcyclohexyl)-1-methylethyl 5-norbornen-2-carboxylate,
1-(4-hydroxycyclohexyl)-1-methylethyl 5-norbornen-2-carboxylate,
1-methyl-1-(4-oxocyclohexyl)ethyl 5-norbornen-2-carboxylate,
1-(1-adamantyl)-1-methylethyl 5-norbornen-2-carboxylate,
1-methylcyclohexyl 5-norbornen-2-carboxylate,
2-methyl-2-adamantyl 5-norbornen-2-carboxylate, In these cases, it is advantageous from the standpoint of dry etching resistance to contain 2-alkyl-2-adamantyl or 1-(1-adamantyl)-1-alkylalkyl as the acid labile group in the resin.

The resin containing a structural unit derived from 2-norbornene shows strong structure because alicyclic group is directly present on its main chain and shows a property that dry etching resistance is excellent. The structural unit derived from 2-norbornene can be introduced into the main chain by radical polymerization using, for example, in addition to corresponding 2-norbornene, aliphatic unsaturated dicarboxylic anhydrides such as maleic anhydride and itaconic anhydride together. The structural unit derived from 2-ethyl-2-adamantyl 5-norbornen-2-carboxylate,
2-hydroxyethyl 5-norbornen-2-carboxylate,
5-norbornen-2-methanol,
5-norbornen-2,3-dicarboxylic acid anhydride, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl(meth)acrylate or 1-(1-adamantyl)-1-alkylalkyl (meth)acrylate are used as the acid-labile group, it is advantageous that the ratio of the structural units is 15% by mol or more in all structural units of the resin.

When, in addition to structural units having an acid-labile group, other structural units not easily dissociated by the action of an acid, for example, a structural unit derived from 3-hydroxy-1-adamantyl(meth)acrylate, a structural units derived from 3,5-dihydroxy-1-adamantyl(meth)acrylate or α- or β-(meth)acryloyloxy-γ-butyrolactone, a structural unit of the formula (VIIa) or (VIIb), a structural unit derived from hydroxystyrene, a structural unit of the formula (VIII), a structural unit derived from maleic anhydride of the formula (IX) which is a structural unit derived from an aliphatic unsaturated dicarboxylic anhydride, a structural unit derived from itaconic anhydride of the formula (X) or the like are contained, it is preferable that the sum of these structural units is in the range of 20 to 90% by mol based on all structural units of the resin.

When 2-norbornenes and aliphatic unsaturated dicarboxylic anhydride are used as copolymerization monomer, it is preferable to use them in excess amount in view of a tendency that these are not easily polymerized.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulae:

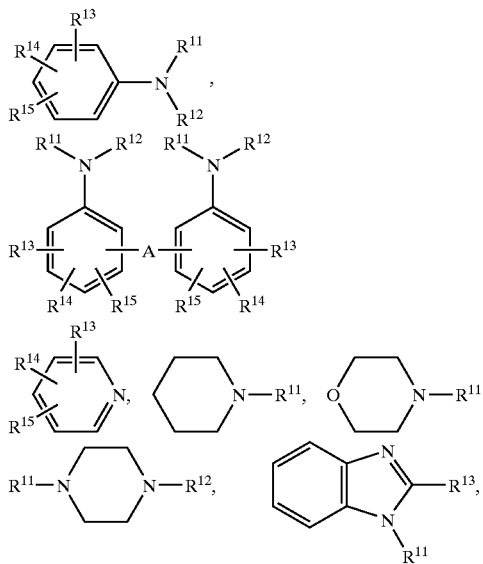

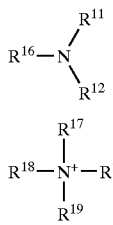

-continued

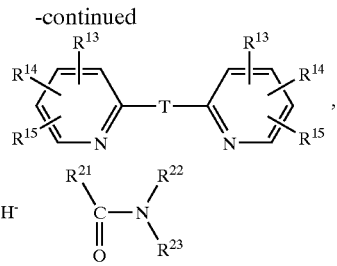

Wherein $R^{11}$ and $R^{12}$ represent each independently hydrogen, alkyl, cycloalkyl or aryl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

$R^{13}$, $R^{14}$ and $R^{15}$ each independently represent hydrogen, alkyl, cycloalkyl, aryl or alkoxy. The alkyl preferably has about 1 to 6 carbon atoms, the cycloalkyl preferably has about 5 to 10 carbon atoms, the aryl preferably has about 6 to 10 carbon atoms, and the alkoxy preferably has about 1 to 6 carbon atoms. Furthermore, at least one hydrogen on the alkyl, cycloalkyl, aryl or alkoxy may each independently be substituted by hydroxyl, amino, or alkoxy having 1 to 6 carbon atoms. At least one hydrogen on the amino may be substituted by alkyl having 1 to 4 carbon atoms.

$R^{16}$ represents alkyl or cycloalkyl. The alkyl preferably has about 1 to 6 carbon atoms, and the cycloalkyl preferably has about 5 to 10 carbon atoms. Furthermore, at least one hydrogen on the alkyl or cycloalkyl may each independently be substituted by hydroxyl, amino, or alkoxy having 1 to 6 carbon atoms. At least one hydrogen on the amino may be substituted by alkyl having 1 to 4 carbon atoms.

$R^{17}$, $R^{18}$, $R^{19}$ and $R^{20}$ each independently represent alky, cycloalkyl or aryl, with the proviso that at least one of them represent alkyl or cycloalkyl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

T represents alkylene, carbonyl, imino, sulfide or disulfide. The alkylene preferably has about 2 to 6 carbon atoms.

$R^{21}$, $R^{22}$ and $R^{23}$ each independently represent hydrogen, alkyl having 1 to 6 carbon atoms, aminoalkyl having 1 to 6 carbon atoms, hydroxyalkyl having 1 to 6 carbon atoms or substituted or unsubstituted aryl having 6 to 20 carbon atoms, or $R^{21}$ and $R^{22}$ bond to form a divalent acyclic hydrocarbon having 3 to 7 carbon atoms which form a ring together with the adjacent —CON($R^{23}$)—.

Moreover, among $R^{11}$–$R^{23}$, in regard to those which can be straight-chained or branched, either of these may be permitted.

Examples of such compounds include hexylamine, heptylamine, octylamine, nonylamine, decylamine, aniline, 2-, 3- or 4-methylaniline, 4-nitroaniline, 1- or 2-naphtylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl] amine, triisopropanolamine, N,N-dimethylaniline, 2,6-isopropylaniline, imidazole, pyridine, 4-methylpyridine, 4-methyimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl) trimethylammonium hydroxide (so-called "choline"), N-methylpyrrolidone, dimethylimidazole, and the like.

Furthermore, hindered amine compounds having piperidine skeleton as disclosed in JP-A-H11-52575 can be used as quencher It is preferable that the present composition contains resin in an amount of about 80 to 99.9% by weight and the sufonate of the formula (I) in an amount of 0.1 to 20% by weight based on the total solid content of the present composition.

When basic compound is used as a quencher, it is preferable that the basic compound is contained in an amount of about 0.01 to 1% by weight based on the total solid content of the present composition.

The present composition can contain, if necessary, various additives in small amount such as a sensitizer, solution suppressing agent, other resins, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used, In the present invention, the total solid content means total content exclusive of solvent(s).

Examples thereof include glycol ether esters such as ethylcellosolve acetate, methylcellosolve acetate, propylene glycol monomethyl ether acetate, and the like; esters such as ethyl lactate, butyl acetate, amyl acetate and ethyl pyruvate, and the like; ketones such as acetone, methyl isobutyl ketone, 2-heptanone, cyclohexanone, and the like; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

RESIN SYNTHESIS EXAMPLE 1 (SYNTHESIS OF RESIN A1)

(1) 39.7 g (0.16 mol) of 2-ethyl-2-adamantyl methacrylate, 103.8 g (0.64 mol) of p-acetoxystyrene and 265 g of isopropanol were charged into a flask and the mixture was heated to 75° C. in a nitrogen atmosphere. To the heated mixture, the solution consisting of 11.05 g (0.048 mol) of dimethyl 2,2-azobis(2-methylpropionate) and 22.11 g of isopropanol was added dropwise. The added mixture was stirred at 75° C. for 0.3 hour and was maintained to heat under reflux for 12 hours. The resultant mixture was diluted by acetone. The diluted mixture was poured into large amount of methanol, and then filtered to obtain copolymer of 2-ethyl-2-adamantyl methacrylate and p-acetoxystyrene in the form of wet cake containing methanol. The weight of the wet cake was 250 g.

(2) Into the flask, 250 g of the wet cake obtained in (1), 10.3 g (0.084 mol) of 4-dimethylaminopyridine and 202 g of methanol were charged, and the mixture was stirred under reflux for 20 hours. After cooled, the reaction mixture was neutralized by 7.6 g (0.126 mol) of glacial acetic acid, and then to the neutralized mixture, large amount of water was added to precipitate polymer The polymer precipitated was filtered, the filtered solid was dissolved in acetone, and the solution was poured into large amount of water to obtain purified polymer. The dissolution and pouring were repeated two more time, and then the polymer was dried to obtain 95.7 g of copolymer of 2-ethyl-2-adamantyl methacrylate and p-hydroxystyrene. The copolymer has a weight average molecular weight of about 8600 and the degree of dispersion was 1.65. The ratio of the structural unit of 2-ethyl-2-adamantyl methacrylate to that of p-hydroxystyrene was determined to be 20 to 80 by $^{13}$C-NMR spectrometer. The copolymer is called as Resin A1.

RESIN SYNTHESIS EXAMPLE 2 (SYNTHESIS OF RESIN A2)

(1) The reaction and post treatments were conducted in the same manner as in Resin synthesis example 1 (1) except that the amounts of 2-ethyl-2-adamantyl methacrylate and p-acetoxystyrene were changed to 59.6 g (0.24 mol) and 90.8 g (0.56 mol), respectively, to obtain 250 g of copolymer of 2-ethyl-2-adamantyl methacrylate and p-acetoxystyrene in the form of wet cake containing methanol.

(2) The reaction and post treatments were conducted in the same manner as in Resin synthesis example 1 (2) except that the amounts of 4-dimethylaminopyridine, methanol and glacial acetic acid were changed to 10.8 g (0.088 mol), 239 g and 8.0 g (0.133 mol), respectively, to obtain 102.8 g of crystals of copolymer of 2-ethyl-2-adamantyl methacrylate and p-hydroxystyrene. The copolymer has a weight average molecular weight of about 8200 and the degree of dispersion was 1.68. The ratio of the structural unit of 2-ethyl-2-adamantyl methacrylate to that of p-hydroxystyrene was determined to be 30 to 70 by $^{13}$C-NMR spectrometer. The copolymer is called as Resin A2.

ACID GENERATOR SYNTHESIS EXAMPLE 1

Synthesis of Acid Generator B1

(1) In a flask, 9.3 g of 2-methyl-2-adamantanol was dissolved in 50 ml of dried N,N-dimethylformamide. To the solution, 2.2 g of 60% NaH was added, and the mixture was stirred at 50° C. for 1.5 hours to obtain Solution A.

Into another flask, 5.0 g of 5-sulfoisophtalic acid monosodium salt was dissolved in 50 ml of N,N-dimethylformamide. To the solution, 6.0 g of carbonyldiimidazole was added, and the mixture was stirred at 25 to 45° C. for 45 minutes. To the stirred mixture, all of Solution A obtained above was added, and the mixture was stirred at 50 to 60° C. for 6 hours. After cooled, to the resultant mixture were added aqueous sodium chloride and chloroform, and extraction and phase separation were performed. The chloroform phase obtained was dried by the addition of anhydrous sodium sulfate. The dried chloroform phase was filtrated, concentrated, and purified by column chromatography to obtain 2.5 g (Yield: 23.8%) of sodium 3,5-di(2-ethyl-2-adamantyloxycarbonyl)benzenesulfonate (hereinafter referred to as "SIPMAD-Na").

(2) Into a flask, 0.8 g of SIPMAD-Na was dissolved in methanol. To the solution, 0.4 g of triphenylsulfonium chloride was added, and the moisture was stirred at a room temperature over a night. The resultant mixture was dissolved in 100 g of ethyl acetate. The solution was washed with 50 g of water, and the washing was repeated 4 more time. The washed solution was concentrated and then to the concentrate, chloroform was added. Then, the solution was again completely concentrated to obtain 0.7 g of a compound (hereinafter referred to as Acid generator B1). It was determined that the structure of Acid generator B1 was the following formula by NMR ("GX-270" manufactured by JEOL Ltd.) and mass spectrometry (LC analyzer is No. 1100 manufactured by HP, MASS analyzer is LC/MSD manufactured by HP).

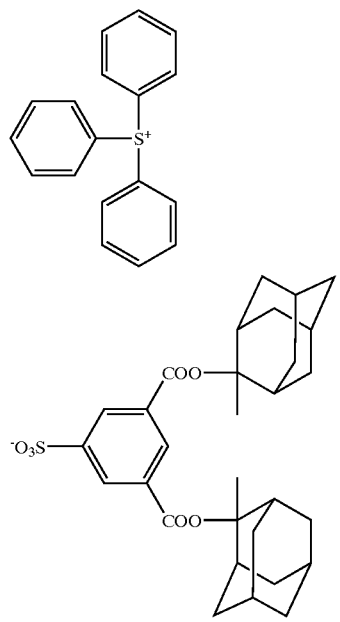

$^1$H-NMR (chloroform-d, internal standard substance: tetramethylsilane): δ (ppm) 1.61–2.04 (m, 24H); 2.42–2.51 (m, 2H); 7.75–7.87 (m, 15H); 8.37 (d, 2H); 8.46 (t, 1H).

MS (ESI (+) Spectrum): M+ 263.1
MS (ESI (−) Spectrum): M− 541.2

ACID GENERATOR SYNTHESIS EXAMPLE 2

Synthesis of Acid Generator B2

The reactions, post treatments and structure determinations were conducted in the same manner as in Acid generator synthesis example 1 except that 2-methyl-2-adamantanol was substituted by 2-ethyl-2-adamantanol to obtain a compound (hereinafter referred to as Acid generator B2). The structure of Acid generator B2) was determined by the following formula.

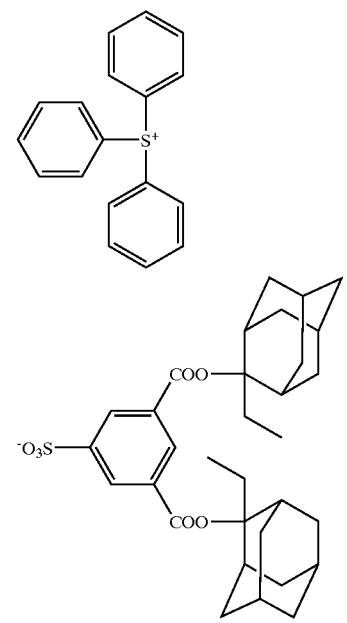

$^1$H-NMR (chloroform-d, internal standard substance: tetramethylsilane): δ (ppm) 0.77 (t, 6H); 1.61–2.02 (m, 24H); 2.27 (q, 4H); 2.48–2.52 (m, 2H); 7.75–7.90 (m, 15H); 8.39 (d, 2H); 8.47 (t, 1H)

MS (ESI (+) Spectrum): M+ 263.0
MS (ESI (−) Spectrum): M− 569.2

ACID GENERATOR SYNTHESIS EXAMPLE 3

Synthesis of Acid Generator B3

The reactions and post treatments were conducted in the same manner as in Acid generator synthesis example 1 except that 5-sulfoisophtalic acid monosodium salt was substituted by 4-sulfobenzoic acid monopotassium salt to obtain a compound (hereinafter referred to as Acid generator B3), and that the structure determination was performed by NMR ("GX-270" manufactured by JEOL Ltd.). The structure of Acid generator B3 was determined by the following formula.

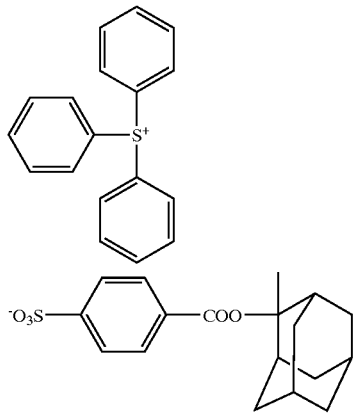

¹H-NMR (chloroform-d, internal standard substance: tetramethylsilane): δ (ppm) 1.57–2.05 (m, 12H); 2.45 (s, 2H); 7.69–7.91 (m, 19H)

ACID GENERATOR SYNTHESIS EXAMPLE 4

Synthesis of Acid Generator B4

Into a flask was charged 16.1 g of cyclohexanol and 60 g of toluene, and 16.0 g of 5-sulfoisophtalic acid was added thereto with stirred, then the mixture was refluxed for dehydration for 6 hours. After cooled, the reaction mixture was concentrated, and 39.5 g of crude diester compound was obtained. To all amount of the diester compound obtained, 220 g of methanol was added, then 7.5 g of silver oxide was added thereto and the mixture was stirred at room temperature for 12 hours. The resultant mixture was filtered twice, and to the filtrate, a solution of 21.7 g of p-tolyldiphenylsulfonium iodide and 217 g of methanol was added with stirred. The stirring was maintained for 12 hours, then the reaction mixture was filtered and concentrated. To the concentrate, 200 g of ethyl acetate was added to prepare ethyl acetate solution. The ethyl acetate solution was washed with 100 g of water three times. The ethyl acetate solution obtained was concentrated. To the concentrate, 200 g of n-heptane was added to wash, then the n-heptane was decanted, and the washed concentrate was concentrated again. The washing, decantation and concentration were repeated six more times. Then, 200 g of n-heptane was added thereto, filtered and dried under reduced pressure to obtain 19.4 g of white crystals (hereinafter referred to as Acid generator B4). The structure of Acid generator B4 was the following formula by NMR ("GX-270" manufactured by JEOL Ltd.).

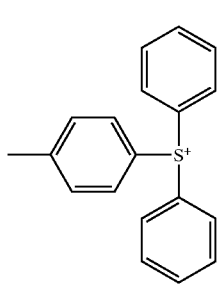

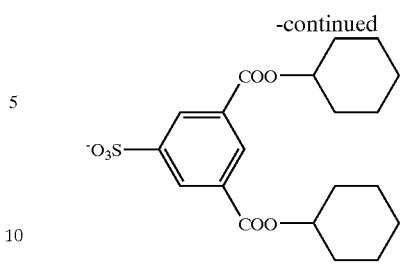

¹H-NMR (chloroform-d, internal standard substance: tetramethylsilane): δ (ppm) 1.19–1.92 (m, 20H); 2.44 (s, 3H); 4.93–5.03 (m, 2H); 7.46 (d, 2H); 7.62–7.78 (m, 12H); 8.63 (t, 2H)

EXAMPLE 1 AND COMPARATIVE EXAMPLE 1

The following components were mixed and dissolved, further, filtrated through a fluorine resin filter having pore diameter of 0.2 μm, to prepare resist liquid.

Resin (in the form of resin solution)
  Resin A1: 5.0 g (as solid content)
  Resin B1: 5.0 g (as solid content)

Acid Generator
  Kind and amount are described in Table 1.

Quencher
  2,6-diisopropylaniline: 0.055 g

Solvent
  Propylene glycol monomethyletheracetate: 232.0 g
  Propylene glycol monomethylether: 58.0 g
  (The amount of solvent includes the amount contained in Resin solution.)

Each of the resist liquids prepared as above was spin-coated over a silicon wafer pretreated with hexamethylsilazane (HMDS), and the silicon wafers thus coated with the respective resist liquids were each prebaked on a proximity hotplate at 120° C. for 60 seconds to form resist film with the thickness of 10 μm.

Using an electron beam drawing apparatus ("HL-800D" manufactured by Hitachi Ltd., 50 keV), each wafer thus formed with the respective resist film was subjected to line and space pattern exposure, with the exposure quantity being varied stepwise.

After the exposure, each wafer was subjected to post-exposure baking on a hotplate at 120° C. for 60 seconds and then to puddle development for 60 seconds with an aqueous solution of 2.38 wt % tetramethylammonium hydroxide.

A cross-sectional view of pattern developed on the silicon wafer was observed with a scanning electron microscope, the results of which are shown in Table 1.

Effective sensitivity: It is expressed as the amount of exposure that the line pattern (light-shielding layer) and the space pattern (light-transmitting layer) become 1:1 after exposure through 0.10 μm line and space pattern mask and development.

Resolution: It is expressed as the minimum size of space pattern which gave the space pattern split by the line pattern at the exposure amount of the effective sensitivity.

Smoothness of pattern wall surface: A pattern wall surface of dense line pattern was observed by a scanning electron microscope, and when line edge roughness is observed, judge is "X" (poor), and when it is not observed, judge is "O" (good).

TABLE 1

| Example No. | Acid Generator & Amount | Effective Sensitivity (mJ/cm$^2$) | Resolution ($\mu$m) | Smoothness of pattern wall surface |
|---|---|---|---|---|
| Example 1 | B1 1.47 g/1.83 mmol | 28.5 | 0.05 | ○ |
| Example 2 | B2 1.52 g/1.83 mmol | 28.4 | 0.06 | ○ |
| Example 3 | B3 1.12 g/1.83 mmol | 23.1 | 0.06 | ○ |
| Comparative Example 1 | B4 1.26 g/1.83 mmol | 32.0 | 0.08 | X |

The sulfonate of the present invention is energy-active, and can be suitably used as a component in a resist. The chemical amplification type positive resist composition of the present invention gives resist patterns having remarkably improved line edge roughness and pattern profile, and also provides excellent resist abilities such as sensitivity, resolution and the like. Therefore, it is suitable for excimer laser lithography and electron beam lithography and the like, has large industrial values.

What is claimed is:

1. A sulfonate of the formula (I):

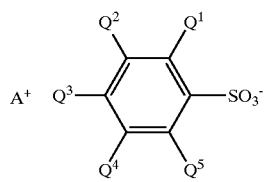

(I)

wherein A$^+$ represents a counter ion and wherein Q$^1$, Q$^2$, Q$^3$, Q$^4$ and Q$^5$ each independently represents a hydrogen, an alkyl having 1 to 16 carbon atoms, an alkoxy having 1 to 16 carbon atoms, a halogen, an aryl having 6 to 12 carbon atoms in which at least one hydrogen may be substituted by an alkyl, a cycloalkyl, an alkoxy, a hydroxyl or a halogen, an arylalkyl having 7 to 12 carbon atoms in which at least one hydrogen on an aryl ring may be substituted by an alkyl, a cycloalkyl, an alkoxy, a hydroxyl or a halogen, a cyano, a mercapto, an alkylthio having 1 to 16 carbon atoms, a hydroxy, a nitro or a group of the formula (I')

—COOR (I')

wherein R represents an aryl having 6 to 12 carbon atoms, a group of the formula (II') or a group of the formula (II")

(II')

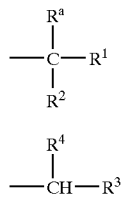

(II")

wherein R$^1$ and R$^2$ each independently represents an alkyl having 1 to 12 carbon atoms, a cycloalkyl having 3 to 12 carbon atoms, an arylalkyl having 7 to 12 carbon atoms or an aryl having 6 to 12 carbon atoms, and at least one hydrogen on an aryl ring in the arylalkyl or in the aryl may be substituted by an alkyl, a cycloalkyl, an alkoxy, a hydroxyl or a halogen, or R$^1$ and R$^2$ bond to form a monocyclic or polycyclic hydrocarbon group together with adjacent —C(R$^a$)—, R$^a$ represents an alkyl having 1 to 8 carbon atoms, and —CH$_2$— in the alkyl except the one at the terminal position may be substituted by —CO—, —O— or —S—, and R$^3$ and R$^4$ each independently represents a hydrogen, an alkyl having 1 to 12 carbon atoms, a cycloalkyl having 3 to 12 carbon atoms, an aryl having 6 to 12 carbon atoms, an arylalkyl having 7 to 12 carbon atoms, at least one hydrogen on the aryl ring in the aryl or in the arylalkyl may be substituted by an alkyl, a cycloalkyl, an alkoxy, a hydroxyl or a halogen, or R$^3$ and R$^4$ bond to form an monocyclic or polycyclic hydrocarbon group together with adjacent —CH—, with the proviso that at least one of Q$^1$, Q$^2$, Q$^3$, Q$^4$ and Q$^5$ is a 1-alkylcycloalkyloxycarbonyl group.

2. The sulfonate according to claim 1, wherein the 1-alkylcycloalkyloxycarbonyl group is a group of the formula (II*)

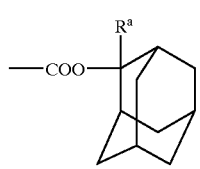

(II*)

wherein R$^a$ has the same meaning as defined above.

3. The sulfonate according to claim 2, wherein R$^a$ in the formula (II*) is a methyl or an ethyl.

4. The sulfonate according to claim 1, wherein A$^+$ is a counter ion of the formula (IIa)

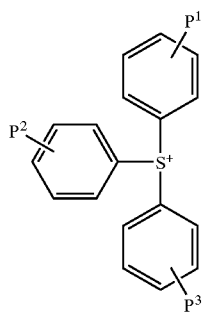

(IIa)

wherein P$^1$, P$^2$ and P$^3$ each independently represents a hydrogen, a hydroxyl, an alkyl having 1 to 6 carbon atoms or an alkoxy having 1 to 6 carbon atoms.

5. The sulfonate according to claim 1, wherein A$^+$ is a counter ion of the formula (IIb)

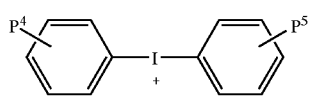

(IIb)

wherein P$^4$ and P$^5$ each independently represents a hydrogen, a hydroxyl, an alkyl having 1 to 6 carbon atoms or an alkoxy having 1 to 6 carbon atoms.

6. The sulfonate according to claim 1, wherein A$^+$ is a counter ion of the formula (IIc)

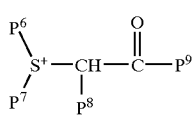

(IIc)

wherein $P^6$ and $P^7$ each independently represents an alkyl having 1 to 6 carbon atoms or a cycloalkyl having 3 to 10 carbon atoms, or $P^6$ and $P^7$ bond to form a divalent acyclic hydrocarbon having 3 to 7 carbon atoms which form a ring together with the adjacent $S^+$, and at least one —$CH_2$— in the divalent acyclic hydrocarbon may be substituted by —CO—, —O— or —S—; $P^8$ represents a hydrogen, $P^9$ represents an alkyl having 1 to 6 carbon atoms, a cycloalkyl having 3 to 10 carbon atoms or an aromatic ring group optionally substituted, or $P^8$ and $P^9$ bond to form 2-oxocycloalkyl together with the adjacent —CHCO—.

7. The sulfonate according to claim 1, wherein $A^+$ is a counter ion of the formula (IId)

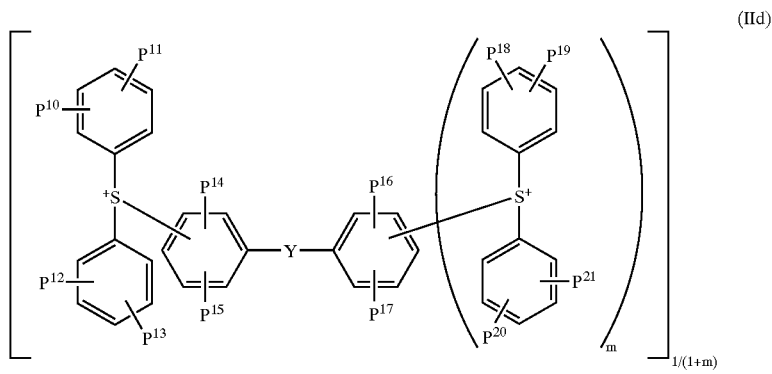

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represents a hydrogen, a hydroxyl, an alkyl having 1 to 6 carbon atoms or an alkoxy having 1 to 6 carbon atoms, Y represents a sulfur or an oxygen, and m represents 0 or 1.

8. A chemical amplification type positive resist composition comprising
a sulfonate of the formula (I):

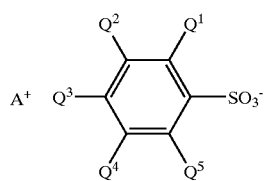

wherein $A^+$ represents a counter ion and wherein $Q^1$, $Q^2$, $Q^3$, $Q^4$ and $Q^5$ each independently represent a hydrogen, an alkyl having 1 to 16 carbon atoms, an alkoxy having 1 to 16 carbon atoms, a halogen, an aryl having 6 to 12 carbon atoms in which at least one hydrogen may be substituted by an alkyl, a cycloalkyl, an alkoxy, a hydroxyl or a halogen, an arylalkyl having 7 to 12 carbon atoms in which at least one hydrogen on an aryl ring may be substituted by an alkyl, a cycloalkyl, an alkoxy, a hydroxyl or a halogen, a cyano, a mercapto, an alkylthio having 1 to 16 carbon atoms, a hydroxy, a nitro or a group of the formula (I')

—COOR (I')

wherein R represents an aryl having 6 to 12 carbon atoms, a group of the formula (II') or a group of the formula (II")

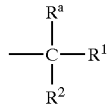

-continued

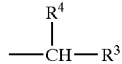

wherein $R^1$ and $R^2$ each independently represents an alkyl having 1 to 12 carbon atoms, a cycloalkyl having 3 to 12 carbon atoms, an arylalkyl having 7 to 12 carbon atoms or an aryl having 6 to 12 carbon atoms, and at least one hydrogen on an aryl ring in the arylalkyl or in the aryl may be substituted by an alkyl, a cycloalkyl, an alkoxy, a hydroxyl or a halogen, or $R^1$ and $R^2$ bond to form a monocyclic or polycyclic hydrocarbon group together with adjacent —C($R^a$)—, $R^a$ represents an alkyl having 1 to 8 carbon atoms, and —$CH_2$— in the alkyl except the one at the terminal position may be substituted by —CO—, —O— or —S—, and $R^3$ and $R^4$ each independently represents a hydrogen, an alkyl having 1 to 12 carbon atoms, a cycloalkyl having 3 to 12 carbon atoms, an aryl having 6 to 12 carbon atoms, an arylalkyl having 7 to 12 carbon atoms, at least one hydrogen on the aryl ring in the aryl or in the arylalkyl may be substituted by an alkyl, a cycloalkyl, an alkoxy, a hydroxyl or a halogen, or $R^3$ and $R^4$ bond to form an monocyclic or polycyclic hydrocarbon group together with adjacent —CH—, with the proviso that at least one of $Q^1$, $Q^2$, $Q^3$, $Q^4$ and $Q^5$ is a 1-alkylcycloalkyloxycarbonyl group; and a resin which contains a structural unit having an acid labile group and which itself is insoluble or poorly soluble in an alkali aqueous solution but becomes soluble in an alkali aqueous solution by the action of an acid.

9. The composition according to claim 8 wherein the content of the structural unit having an acid-labile group in all structural units of the resin is from 10 to 80% by mol.

10. The composition according to claim 9 wherein the resin further contains a structural unit derived from 2-norbornene and a structural unit derived from an aliphatic unsaturated dicarboxylic anhydride.

11. The composition according to claim 8 wherein the structural unit having an acid-labile group is a structural unit derived from 2-alkyl-2-adamantyl (meth)acrylate or 1-(1-adamantyl)-1-alkylalkyl(meth)acrylate.

12. The composition according to claim 8 wherein the resin contains, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl (meth)acrylate, a structural unit derived from (meth)acryloyloxy-γ-butyrolactone having a lactone ring optionally substituted by alkyl, a structural unit of the formula (VIIa) and a structural unit of the formula (VIIb)

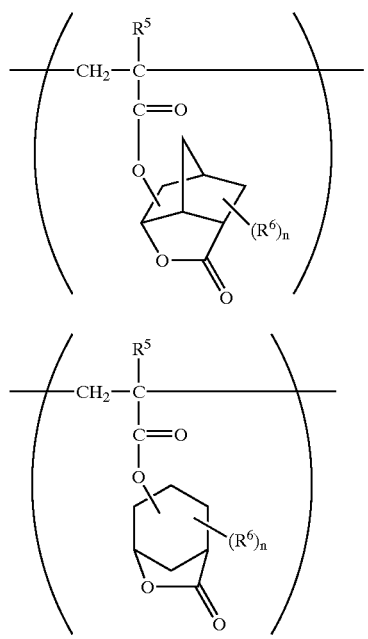

wherein $R^5$ represents a hydrogen, a methyl or a trifluoromethyl and $R^6$ represents a methyl or a trifluoromethyl, and n represents an integer of 0 to 3.

13. The composition according to claim 8 wherein the composition further comprises a basic nitrogen-containing organic compound as a quencher.

14. The composition according to claim 8 wherein the composition further comprises a surfactant.

15. The composition according to claim 8 wherein, in the formula (I), $A^+$ is a counter ion of the formula (IIa), the formula (IIb), the formula (IIc) or the formula (IId):

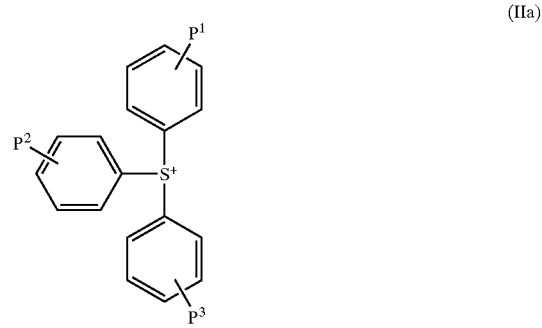

wherein $P^1$, $P^2$ and $P^3$ each independently represents a hydrogen, a hydroxyl, an alkyl having 1 to 6 carbon atoms or an alkoxy having 1 to 6 carbon atoms;

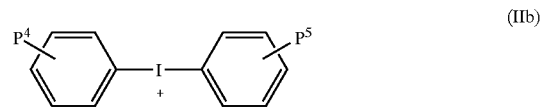

wherein $P^4$ and $P^5$ each independently represents a hydrogen, a hydroxyl, an alkyl having 1 to 6 carbon atoms or an alkoxy having 1 to 6 carbon atoms;

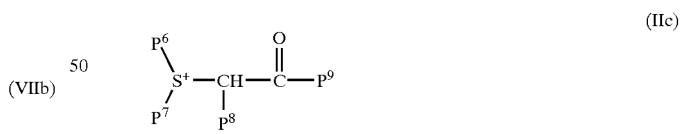

wherein $P^6$ and $P^7$ each independently represents an alkyl having 1 to 6 carbon atoms or a cycloalkyl having 3 to 10 carbon atoms, or $P^6$ and $P^7$ bond to form a divalent acyclic hydrocarbon having 3 to 7 carbon atoms which form a ring together with the adjacent $S^+$, and at least one —$CH_2$— in the divalent acyclic hydrocarbon may be substituted by —CO—, —O— or —S—; $P^8$ represents a hydrogen, $P^9$ represents an alkyl having 1 to 6 carbon atoms, a cycloalkyl having 3 to 10 carbon atoms or an aromatic ring group optionally substituted, or $P^8$ and $P^9$ bond to form 2-oxocycloalkyl together with the adjacent —CHCO—;

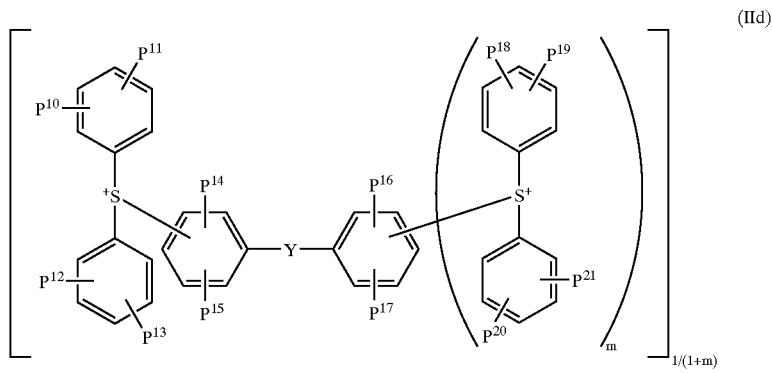

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ independently represents a hydrogen, a hydroxyl, an alkyl having 1 to 6 carbon atoms or an alkoxy having 1 to 6 carbon atoms, Y represents a sulfur or an oxygen, and m represents 0 or 1.

16. The composition according to claim 8, wherein the 1-alkylcycloalkyloxycarbonyl group is a group of the formula (II*)

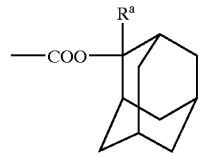

wherein $R^a$ has the same meaning as defined above.

17. The composition according to claim 16, wherein $R^a$ in the formula (II*) is a methyl or an ethyl.

* * * * *